(12) United States Patent
Tsuchiya et al.

(10) Patent No.: US 8,092,795 B2
(45) Date of Patent: *Jan. 10, 2012

(54) LIQUID SEASONING

(75) Inventors: Shigemi Tsuchiya, Sumida-ku (JP);
Youko Seo, Sumida-ku (JP); Jun Kohori, Sumida-ku (JP)

(73) Assignee: Kao Corporation, Tokyo (JP)

(*) Notice: Subject to any disclaimer, the term of this patent is extended or adjusted under 35 U.S.C. 154(b) by 63 days.

This patent is subject to a terminal disclaimer.

(21) Appl. No.: 12/637,530

(22) Filed: Dec. 14, 2009

(65) Prior Publication Data

US 2010/0092649 A1 Apr. 15, 2010

Related U.S. Application Data

(62) Division of application No. 11/271,790, filed on Nov. 14, 2005, now Pat. No. 7,666,409.

(30) Foreign Application Priority Data

Nov. 16, 2004 (JP) .................. 2004-332501
Nov. 16, 2004 (JP) .................. 2004-332502

(51) Int. Cl.
*A61K 9/00* (2006.01)
*A61K 35/00* (2006.01)
*A61K 31/198* (2006.01)
*A61K 47/00* (2006.01)
*A23D 9/013* (2006.01)
*A23L 1/221* (2006.01)
*A23J 1/00* (2006.01)
*A01N 61/00* (2006.01)

(52) U.S. Cl. ........ 424/115; 424/400; 424/439; 426/531; 426/650; 426/656; 514/1; 514/566

(58) Field of Classification Search .................. None
See application file for complete search history.

(56) References Cited

U.S. PATENT DOCUMENTS

| 4,593,045 A | 6/1986 | Flork et al. |
| 5,562,942 A | 10/1996 | Koh et al. |
| 6,159,529 A | 12/2000 | Uchida et al. |
| 6,379,717 B1 | 4/2002 | Hatori |
| 6,458,392 B1 | 10/2002 | Okawa et al. |
| 6,730,335 B1 | 5/2004 | Indoh et al. |
| 7,666,409 B2 * | 2/2010 | Tsuchiya et al. ............. 424/115 |
| 7,727,524 B2 * | 6/2010 | Tsuchiya et al. ............. 424/115 |
| 7,887,868 B2 * | 2/2011 | Tsuchiya et al. ............. 426/589 |
| 2002/0054923 A1 | 5/2002 | Suzuki et al. |
| 2003/0003212 A1 | 1/2003 | Chien et al. |
| 2005/0123670 A1 | 6/2005 | Vasquez |

FOREIGN PATENT DOCUMENTS

| JP | 59-55165 | 3/1984 |
| JP | 2-167052 | 6/1990 |
| JP | 5-7987 | 1/1993 |
| JP | 5-219915 | 8/1993 |
| JP | 6-78716 | 3/1994 |
| JP | 6-133723 | 5/1994 |
| JP | 6-197727 | 7/1994 |
| JP | 6-97972 | 12/1994 |
| JP | 2675254 | 7/1997 |
| JP | 10-66540 | 3/1998 |
| JP | 11-187841 | 7/1999 |
| JP | 2000-60489 | 2/2000 |
| JP | 2001-245627 | 9/2001 |
| JP | 2002-87977 | 3/2002 |
| JP | 2002-142715 | 5/2002 |
| JP | 2002-165577 | 6/2002 |
| JP | 2002-345430 | 12/2002 |
| JP | 2004-147560 | 5/2004 |
| JP | 2004-194515 | 7/2004 |
| JP | 2004-290088 | 10/2004 |
| JP | 2004-290129 | 10/2004 |

OTHER PUBLICATIONS

Tochikura, T., "Science and Technology of Soy Sauce", published by Brewing Society of Japan, Mar. 30, 1988, pp. 406-409.

Nakamura, M., et al., "Feasability and Effect of Blood Pressure of 6-Week Trial of Low Sdium Soy Sauceand Miso (Fermented Soybean Paste)", Circulation Journal. 2003, 67, pp. 530-534.

YAMASA "Naturally Brewed YAMASA Less Salt Soy Sauce"Yamasa Corporation USA <http://www.yamasausa.com/Yamasa_products_retail.htm>Oct. 3, 2003 (accessed online archive Aug. 16, 2007), 5 pages.

Yamaguchi, Shizuko and Ninomiya Kumiko. "The Use and Utility of Glutamates as Flavoring Agens in Food: Umami and Food Palatability", Journal of Nutrition. 2000, 130, pp. 921S-926S.

Ajinomoto, :Food and Amino Acids Encyclopedia of Amino Acids. <http://web.archive.org/web/20030812102616/http://www.ajinomoto.com/amino/eng/food.html> archived online Aug. 12, 2003 (Accessed Feb. 28, 2008), 3 pages.

Cotner, Sam. "Organic Compounds" Plant Tissue Culture Network <http://web.archive.prg/web/20010522165515/http://aggie-horticulure.tamu.edu/tisscult/database/media/organic.html> archived online May 22, 2001 (accessed Mar. 28, 2008), 3 pages.

Notice of Reasons for Rejection issued on Nov. 25, 2008, in Japanese Patent Application No. 2004-332501 (with English Translation), 6 pages.

Written Submisson of Publications filed on Aug. 12, 2008, in Japanese Patent Application No. 2004-332501 (with English Translation), 26 pages.

* cited by examiner

*Primary Examiner* — Chris R Tate
*Assistant Examiner* — Aaron J Kosar
(74) *Attorney, Agent, or Firm* — Oblon, Spivak, McClelland, Maier & Neustadt, L.L.P.

(57) ABSTRACT

The present invention provides a liquid seasoning, which brings on a sufficient salty taste although it has a low common salt concentration, and which exhibits for example a pharmacological effect such as an antihypertensive effect at a high level. The present invention relates to a liquid seasoning, which contains the following components (A) to (C):

(A) 3.55% or less by weight of sodium;
(B) 0.5% to 4.2% by weight of potassium; and
(C) 0.1% to 10% by weight of a food material having an antihypertensive effect, wherein the remaining portion of the liquid seasoning excluding component (C) is adapted by incorporation of a substance other than component (C) to have a nitrogen content (D) of 1.6% or more based on the total weight of the liquid seasoning.

10 Claims, 3 Drawing Sheets

LIQUID SEASONING

CROSS REFERENCES TO RELATED APPLICATIONS

This application is a Divisional Application of U.S. patent application Ser. No. 11/271,790, filed on Nov. 14, 2005 now U.S. Pat. No. 7,666,409, and claims priority to Japanese Patent Application 2004-332501, filed on Nov. 16, 2004, and Japanese Patent Application No. 2004-332502, filed on Nov. 16, 2004.

BACKGROUND OF THE INVENTION

1. Field of the Invention

The present invention relates to a liquid seasoning.

2. Background of the Invention

Nowadays, interest in physiological functions of various components contained in food products is highly increasing. The Ministry of Health, Labor, and Welfare in Japan has certified food products containing components associated with such physiological functions or biological activities as Food for Specified Health Use (FOSHU). Such food products have been commercialized in the form of a beverage, yoghurt, soup, miso soup, a prepared food product such as hamburger steak, a tablet-form confectionery, a tablet, or the like. It has been recommended that such food products be ingested once or twice a day.

Various materials have been proposed as materials having physiologically active functions. An example is a food material having an antihypertensive effect. Among others, peptide, γ-aminobutyric acid, chlorogenic acid, or the like are considered to be substances that are contained in food products and are highly safe. Thus, techniques of increasing the contents of such substances in food products or adding such substances to food products have been proposed (JP-A-06-78716, JP-A-06-197727, JP-A-2000-60489, and JP-A-2004-147560).

Since ingestion of common salts has adverse effects on renal diseases, cardiac diseases, and hypertension, addition of these to food products containing a high content of salts has been proposed. There have been a large number of techniques regarding the combined use of such a food material having an antihypertensive effect with soy sauce as a representative example of the aforementioned food products (JP-A-2002-87977, JP-A-2004-290129, JP-A-2004-194515; JP-A-2004-290088, JP-A-06-133723, and JP-A-02-167052). In order to ingest an effective amount of such a food material, a large amount of the food product should be ingested. However, ingestion of a large amount of such a food product results in ingestion of large quantities of salts. This leads to a decrease in the effect of ingesting the aforementioned food material, and thus it is unfavorable. Further, addition of a large amount of the aforementioned food material may affect the flavor of the food product.

SUMMARY OF THE INVENTION

The present invention provides a liquid seasoning, which contains the following components (A) to (C):
(A) 3.55% or less by weight of sodium;
(B) 0.5% to 4.2% by weight of potassium; and
(C) 0.05% to 10% by weight of a food material having an antihypertensive effect,
wherein the remaining portion of the liquid seasoning excluding component (C) is adapted by incorporation of a substance other than component (C) to have a nitrogen content (D) of 1.6% or more based on the total weight of the liquid seasoning.

DETAILED DESCRIPTION OF THE INVENTION

Figure 1:
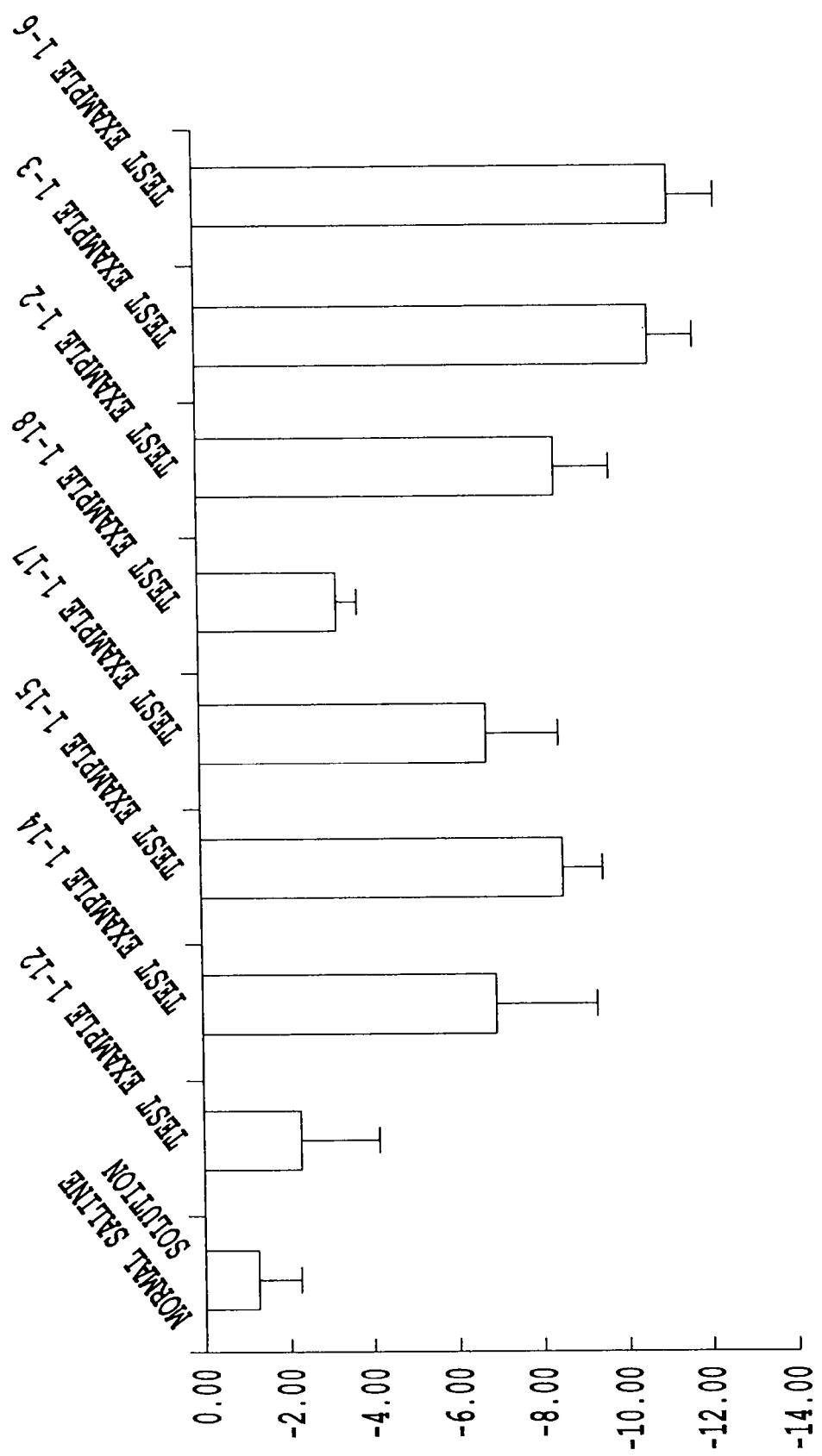
FIG. 1 shows the rate of change (%) of the rat systolic blood pressure, which was measured 6 hours after ingestion of the liquid seasoning of the present invention.

In the aforementioned prior art techniques, a problem regarding flavor that occurs when a food material having an antihypertensive effect is used with the combination of a food product containing high quantities of common salts, and a problem regarding ingestion of high quantities of common salts that occurs when such a food product is ingested in high volume, have not yet been solved. Hence, it is still considered difficult to continuously ingest the aforementioned food product. When the aforementioned food material is used with the combination of low salt food products including low salt soy sauce as a typical example, the obtained food product is poor in terms of salty taste, and thus an object regarding the enhancement of salty taste arises. There have been various techniques of improving the flavor of such a low common salt food product (JP-B-2675254, JP-B-06-97972, JP-A-10-66540, JP-A-2001-245627, JP-A-2002-165577, JP-B-05-007987, and JP-A-11-187841), and these techniques bring on certain effects. However, it cannot be said that such effects are sufficient. In particular, it cannot be said that such effects can sufficiently be obtained in terms of a good balance between a decrease in the common salt concentration and the maintenance of a salty taste.

Accordingly, the present invention provides a liquid seasoning produced by combining a liquid seasoning including soy sauce ingested on a daily basis as a typical example with a food material having an antihypertensive effect, which improves the flavor, facilitates continuous ingestion, and exhibits for example a pharmacological effect such as an antihypertensive effect at a high level.

With regard to a liquid seasoning containing a food material having an antihypertensive effect, the present inventors have conducted studies regarding a means for improving the flavor and also bringing on a salty taste although the sodium concentration thereof is set at 9% or less by weight (the common salt concentration thereof is set at 9% or less by weight). As a result, the inventors have found that a system containing 3.55% or less by weight of sodium (9% or less by weight of common salt), 0.5% to 4.2% by weight of potassium, and a predetermined amount or more of nitrogen, so as to obtain a liquid seasoning, whose flavor is not deteriorated although a food material having an antihypertensive effect is added thereto, and brings on a stronger salty taste and good taste. The inventor has also found that this liquid seasoning may be continuously ingested and has an effective antihypertensive effect.

The present invention provides a liquid seasoning containing 3.55% or less by weight of sodium (9% or less by weight of common salt), whose flavor is not deteriorated although a food material having an antihypertensive effect is added thereto, and which brings on a sufficiently strong salty taste, facilitates continuous ingestion, and exhibits a pharmacological effect such as an antihypertensive effect at a high level. The liquid seasoning of the present invention is useful as a low salt soy souse.

The term "low salt soy sauces" is used in the present application to mean "soy sauce" and "soy sauce processed food," wherein the sodium content in 100 g of such a product is 3,550 mg or less (9 g of common salts). Thus, this term is not limited to a special use food for patients defined by the Nutrition Improvement Law of JAPAN. The term "soy sauce" is a liquid seasoning defined by the Japanese Agricultural Standard (JAS), and the term "soy sauce processed food" is also a liquid seasoning, which is produced by adding a seasoning, an acidulant, a flavor, a broth, extracts, etc., to the soy sauce that complies with the Japanese Agricultural Standard (JAS), and which is used for the same purpose as that of "soy sauce." Herein, the term "soy sauce" used in the present application has the same concept as that of the "soy sauce" defined by the Japanese Agricultural Standard (JAS). In addition, the term "liquid seasoning" used in the present application has a concept, which includes low salt soy sauce and seasonings that comply with the requirements of the present application, although they deviate from standards as the aforementioned low salt soy sauces. In the field of liquid seasoning manufacturing, the content of a mixed substance is generally indicated by w/v %. In the present application, however, the amount of each component mixed is indicated by % by weight based on the total weight of a liquid seasoning. In this case, in the case of a nitrogen content in soy sauce for example, "1.6% by weight" corresponds to "1.9 w/v %."

The content of sodium (A) in the liquid seasoning of the present invention is set at 3.55% or less by weight. However, it is preferably between 2.75% and 3.5% by weight, and more preferably between 3.1% and 3.4% by weight, in terms of the antihypertensive effect and flavor (sufficient salty taste). It is to be noted that the term "content" is used in the present invention to mean the ratio of a component in the total amount of the liquid seasoning, unless otherwise specified. The common salt may be used as sodium (A) in the liquid seasoning of the present invention. The content of common salt in the liquid seasoning of the present invention is set at 9% or less by weight. It is preferably between 7% and 9% by weight, and more preferably between 8% and 9% by weight, in terms of the antihypertensive effect and flavor (sufficient salty taste).

The content of potassium (B) in the liquid seasoning of the present invention is set between 0.5% and 4.2% by weight. However, in order to increase the salty taste in spite of a low sodium content and to prevent a bitter taste, it is preferably between 1% and 3.6% by weight, and more preferably between 1.5% and 3.1% by weight. In addition, potassium chloride is preferably used as such potassium because it has a salty taste and a very little extent of abnormal taste. When potassium chloride is used, it is mixed to a liquid seasoning at a weight ratio between 1% and 7% by weight, preferably between 2% and 6% by weight, and more preferably between 3% and 5% by weight, based on the total weight thereof.

In order to adjust the content of sodium and that of potassium to the aforementioned ranges, the following methods may be applied, for example: a method of producing soy sauce using a mixed solution consisting of common salt and potassium chloride as mother water; a method of mixing soy sauce obtained using only a potassium chloride solution as mother water, with soy sauce obtained using only a saline solution as mother water; and a method of subjecting common soy sauce obtained using a saline solution as mother water to electrodialysis or membrane treatment, so as to eliminate sodium, and then adding potassium chloride to the desalted soy sauce.

A food material (C) having an antihypertensive effect in the liquid seasoning of the present invention is preferably one or more selected from the group consisting of polyphenols, a peptide having angiotensin converting enzyme inhibitory activity, and a sympathoinhibitory substance.

Specifically, such polyphenols may preferably be phenol substances, to the benzene ring of which, one or more, and preferably two or more hydroxy groups are bound. Examples of such substances include flavonoid, tannin, and phenolic acid, which are derived from plants. In addition, glycosides of these substances may also be used. More preferred examples of polyphenols include caffeoylquinic acids, feruloylquinic acid, flavonols, flavanols, flavanones, flavones, isoflavones, and anthocyanidins. Specific examples include catechin, epicatechin, gallocatechin, epigallocatechin, rutin, quercitrin, isoquercitrin, quercetin, myricitrin, myricetin, daizein, daizin, glycitein, glycitin, genistein, genistin, myricitrin, myricetin, hesperidin, methylhesperidin, neohesperidin, hesperetin, naringin, naringenin, prunin, astragalin, kaempferol, apiin, apigenin, delphinidin, delphin, nasunin, peonidin, peonin, petunin, peonidin, malvidin, malvin, enin, cyanidin, leucocyanidin, cyanin, chrysanthemin, keracyanin, idein, mecocyanin, pelargonidin, callistephin, a derivative thereof, and a mixture consisting of two or more selected from among the aforementioned substances. Examples of such a derivative include an acetylated product, a malonylated product, a methylated product, and a sugar-binding product. As a preferred example of such a sugar-binding product, one or more molecules of sugars, such as glucose, rhamnose, galactose, rutinose, neohesperidose, or apiosyl glucose, bind to one molecule of polyphenol via a covalent bond. Preferably 1 to 20, more preferably 2 to 10 molecules of such sugars bind to the above polyphenol. Of these, caffeoylquinic acids are preferable because they have a stable and permanent antihypertensive effect. In addition, the polyphenols in the present invention includes the compounds which substituted a part or all of the methoxyl groups for hydroxy groups in the polyphenol molecules.

Such caffeoylquinic acids include isomers and analogs. In the present invention, pure isomers, analogs, or mixtures thereof may be used. Specific examples of caffeoylquinic acids used in the present invention include 3-caffeoylquinic acid, 4-caffeoylquinic acid, 5-caffeoylquinic acid (chlorogenic acid), 3,4-dicaffeylquinic acid, 3,5-dicaffeylquinic acid, 4,5-dicaffeylquinic acid, 3-ferulylquinic acid, 4-ferulylquinic acid, 5-ferulylquinic acid, and 3-ferulyl-4-caffeoylquinic acid.

When caffeoylquinic acids are converted into salts, they are able to improve water solubility and thereby increase physiological effectiveness. Such salts are preferably pharmacologically acceptable salts. Examples of a basic substance used for forming such salts include: alkaline metal hydroxides such as lithium hydroxide, sodium hydroxide, or potassium hydroxide; alkaline-earth metal hydroxides such as magnesium hydroxide or calcium hydroxide; inorganic bases such as ammonium hydroxide; basic amino acids such as arginine, lysine, histidine, or ornithine; and organic bases such as monoethanolamine, diethanolamine, or triethanolamine. Of these, alkaline metal hydroxides or alkaline-earth metal hydroxides are preferable. In the present invention, these salts may be first prepared, and the prepared salts may be then added to a composition consisting of other components. Otherwise, caffeoylquinic acids and a salt-forming substance may be added to the aforementioned composition separately, and thereafter, salts may be formed therein.

Natural product extracts containing caffeoylquinic acids, and plant extracts containing caffeoylquinic acids, are preferably extracted from plants containing large quantities of caffeoylquinic acids, such as coffee, cabbage, lettuce, artichoke, tomato, eggplant, potato, carrot, apple, pear, plum, peach, apricot, cherry, sunflower, Jew's marrow, or sweet potato.

Specifically, as a green coffee bean extract, "Flavor Holder" manufactured by T. Hasegawa Co., Ltd. may be used. As an apple extract, "Applephenon" manufactured by the Nikka Whisky Distilling Co., Ltd. may be used. As a sunflower seed extract, "Heliant S-100" manufactured by Dainippon Ink and chemicals, Inc. may be used. The contents of such caffeoylquinic acids in the used plant extract are preferably between 1% and 80% by weight, more preferably between 1% and 50% by weight, and even more preferably between 1% and 40% by weight, in terms of the antihypertensive effect.

Isoflavone extracted from soy beans may preferably be used. As isoflavone that can be easily dissolved in the liquid seasoning, glycosides such as prunetin (5,4'-dihydroxy-7-methoxy body) or irigenin (5,7,3'-trihydroxy-6,4',5'-trimethoxy body) may preferably be used.

The amount of polyphenols mixed into the liquid seasoning of the present invention is preferably between 0.1% and 5% by weight, more preferably between 0.2% and 3% by weight, and even more preferably between 0.5% and 2% by weight, in terms of the antihypertensive effect and flavor. Herein, the amount of polyphenols mixed means the amount of polyphenols added to the liquid seasoning. If the amount of polyphenol is less than 0.1% by weight, sufficient antihypertensive effect cannot be obtained. In contrast, if the amount of polyphenol is more than 5% by weight, it is not preferable because it results in a strong abnormal taste.

As a peptide having angiotensin converting enzyme inhibitory activity, those derived from food product materials may be used. In particular, a peptide derived from milk, a peptide derived from cereal, and a peptide derived from fish, are preferable. Herein, as a peptide derived from cereal, a peptide derived from cereal having a molecular weight between 200 and 4,000, and a peptide derived from corn having a molecular weight between 200 and 4,000, are preferable. Moreover, a peptide with a molecular weight between 200 and 4,000 obtained by treating a corn protein, soybean protein, wheat protein, or the like with protease, and particularly, a peptide with a molecular weight between 200 and 4,000 obtained by treating a corn protein with alkaline protease, are preferable (JP-A-7-284369). As a peptide derived from fish, a peptide derived from fish with a molecular weight between 200 and 10,000 is preferable. A peptide with a molecular weight between 200 and 10,000, which is obtained by treating fish such as mackerel, oceanic bonito, tuna, or saury with protease, may be more preferably used. Even more preferably, a peptide with a molecular weight between 200 and 10,000, which is obtained by treating a bonito protein with protease, may be used.

The strength of angiotensin converting enzyme inhibitory activity is indicated by a concentration necessary for inhibiting 50% of the angiotensin converting enzyme activity (IC50). When the IC50 of a peptide having angiotensin converting enzyme inhibitory activity used in the present invention is approximately between 50 and 1,000 μg/ml, it may be anticipated that the peptide exhibits an antihypertensive effect in a low salt soy sauce system.

Examples of a commercially available peptide product that may be used in the present invention include: Peptino (Nihon Shokuhin Kako Co., Ltd.; IC50: 130 μg/ml) that is a peptide derived from corn; Glutamine Peptide GP-1 (Nisshin Pharma; IC50: 508 μg/ml) that is a peptide derived from wheat; Hinute (Fuji Oil Co., Ltd.; IC50: 455 μg/ml) that is a peptide derived from soybeans; and Peptide Straight (Nippon Supplement, Inc.; IC50: 215 μg/ml) that is a peptide derived from oceanic bonito.

The angiotensin converting enzyme inhibitory activity of the above peptide may be measured, using ACE Color (Fujirebio Inc.) that is a measurement kit, which is easily handled and has good repeatability using the synthetic substrate p-hydroxybenzoyl-glycyl-L-histidyl-L-leucine. The amount of the above peptide added is preferably between 0.5% and 20% by weight, more preferably between 1% and 10% by weight, and even more preferably between 2% and 5% by weight, based on the total weight of the liquid seasoning, in terms of the antihypertensive effect and flavor.

Examples of a sympathoinhibitory substance used herein include γ-aminobutyric acid, taurine, and salts thereof. As such γ-aminobutyric acid, not only γ-aminobutyric acid extracted from food products, but also a product produced by allowing decarboxylase to act on L-glutamic acid-containing food products, may preferably be used. Fish sauce broth, a pressed liquid thereof, and a fermented product from such fish sauce broth, may preferably be used for the liquid seasoning. Moreover, products obtained from fermented soybeans, rice germ, and rice bran may preferably be used for the liquid seasoning of the present invention because such products do not impair the flavor thereof. Furthermore, under current circumstances, γ-aminobutyric acid with a purity of 100% may also be obtained by extraction and purification from a crude product obtained as a result of fermentation. Such γ-aminobutyric acid with a purity of 100% may preferably be used because it does not impair the flavor. The amount of γ-aminobutyric acid added is preferably between 0.05% and 5% by weight, more preferably between 0.2% and 3% by weight, and even more preferably between 0.5% and 2% by weight, based on the total weight of the liquid seasoning of the present invention, in terms of the antihypertensive effect and flavor.

Taurine extracted from food products (fish and shell fish meat) may preferably be used. The amount of taurine added is preferably between 0.05% and 5% by weight, more preferably between 0.2% and 3% by weight, and even more preferably between 0.5% and 2% by weight, based on the total weight of the liquid seasoning of the present invention, in terms of the antihypertensive effect and flavor.

In the liquid seasoning of the present invention, it is preferable that the remaining portion of the liquid seasoning excluding component (C) has a nitrogen content (D) of 1.6% or more based on the total weight of the liquid seasoning, because it does not decrease flavor although a food material having an antihypertensive effect is mixed thereto, and also because it increases the salty taste in spite of a low sodium or common salt content and it does not generate a bitter taste. In addition, the nitrogen content is more preferably between 1.6% and 2% by weight. In general, a high nitrogen content in soy sauce results in a mild taste, thereby decreasing the salty taste. However, it has been quite unexpected that the salty taste of soy sauce containing a low concentration of sodium or common salt and potassium can be improved when the total nitrogen content therein is adjusted to the aforementioned range.

The nitrogen content of a common soy sauce is between 1.2% and 1.6% by weight. The nitrogen content of 1.6% or more by weight may be achieved by adding a substance containing nitrogen, such as amino acid, to soy sauce conventionally fermented within the range defined in the present invention, or by subjecting the above soy sauce to a concentration and desalination step. For example, there may be applied: a method, which includes eliminating sodium or common salt by a salt-reduction concentration method, and at the same time, adjusting the dilution rate in volatile components containing water as a main component; or a method of simultaneously concentrating nitrogen, utilizing the transition of ion-bounded water that occurs during elimination of common salt with an electrodialysis device; and other methods. Moreover, there may also be applied: a method of increasing the nitrogen content by concentrating with RO membrane or vacuum concentration, low salt soy sauce with a lower common salt concentration than those of ordinary products; a method of desalting soy sauce with a high nitrogen content, such as tamari soy sauce or re-mashed soy sauce; and other methods (Enhanced: Science and technology of soy sauce, Tatsurokuro Tochikura, published by Brewing Society of Japan, 1994).

As a method of increasing the nitrogen content of the liquid seasoning according to the present invention, a method of adding a substance containing nitrogen other than component (C) is preferable. Among such nitrogen-containing substances other than component (C), amino acids, and in particular, acidic amino acids and basic amino acids are preferable, in terms of an increase in salty taste and duration thereof. The content of acidic amino acid in the liquid seasoning is preferably more than 2% by weight, and/or the content of basic amino acid therein is preferably more than 1% by weight. In addition, the content of acidic amino acid is preferably more than 2% to 5% by weight, more preferably between 2.4% and 4.5% by weight, and even more preferably between 2.5% and 3.8% by weight, in terms of the duration of salty taste. The content of basic amino acid is preferably more than 1% to 3% by weight, more preferably between 1.2% and 2.5% by weight, and even more preferably between 1.5% and 2% by weight, in terms of the duration of salty taste. Moreover, the liquid seasoning of the present invention is preferably based on a fermented seasoning, in terms of the duration of salty taste, flavor, and the like. In such a case, amino acid(s) include those derived from the raw material soy sauce, and in a case where the content of such amino acids is less than the aforementioned ranges, acidic amino acid salts, basic amino acid salts, or the like are preferably added, separately. The term "acidic amino acid and/or basic amino acid" is used in the present invention to mean free amino acids or amino acids that are in the form of amino acid salts. The content of amino acid indicates a value relative to free amino acid in the present invention.

Moreover, in the liquid seasoning of the present invention, among acidic amino acids and/or basic amino acids, aspartic acid and glutamic acid as acidic acids are preferable in terms of the duration of salty taste. The combined use of aspartic acid with glutamic acid is more preferable in terms of the duration of salty taste. In this case, the content of aspartic acid is preferably between 1% and 3% by weight, more preferably between 1.2% and 2.5% by weight, and even more preferably between 1.2% and 2% by weight, in terms of the duration of salty taste. When the liquid seasoning is based on a fermented seasoning, such aspartic acid also includes those derived from the raw material. When the content of aspartic acid is less than the aforementioned range, L-aspartic acid, sodium L-aspartate, or the like are preferably added, separately. On the other hand, the content of glutamic acid is preferably between 1% and 2% by weight, more preferably between 1.2% and 2% by weight, and even more preferably between 1.3% and 1.8% by weight, in terms of the duration of salty taste. When the liquid seasoning is based on a fermented seasoning, such glutamic acid also includes those derived from the raw material. When the content of glutamic acid is less than the aforementioned range, L-glutamic acid, sodium L-glutamate, or the like are preferably added, separately.

Examples of basic amino acid include lysine, arginine, histidine, and ornithine. Of these, lysine and histidine are preferable, and histidine is more preferable. The content of lysine is preferably between 0.5% and 1% by weight in terms of the feeling of stimulation of a salty taste. The content of histidine is preferably between 0.2% and 2% by weight, and more preferably between 0.5% and 1% by weight, in terms of an increase in salty taste and the duration thereof. When the liquid seasoning is based on a fermented seasoning, these basic amino acids also include those derived from the raw material. When the content of the basic amino acid is less than the aforementioned range, it is preferably added separately.

In the liquid seasoning of the present invention, in particular, the weight ratio of aspartic acid/potassium (B) is preferably 0.25 or greater, more preferably 0.3 or greater, even more preferably 0.46 or greater, and even more preferably 0.5 or greater, in terms of the elimination of the bitter taste caused by potassium chloride.

In addition, in the liquid seasoning of the present invention, the remaining portion of the liquid seasoning excluding component (C) preferably has a weight ratio of aspartic acid/nitrogen (D) of 0.5 or greater. The weight ratio is more preferably 0.6 or greater, and even more preferably 0.7 or greater, in terms of an increase in the salty taste and the improvement of sharpness of the taste.

Moreover, in order to set the nitrogen content (D) at 1.6% or more by weight, the liquid seasoning of the present invention may also contain one or more selected from among a nucleic acid seasoning, a protein, a protein hydrolysate, or the like.

Examples of a nucleic acid seasoning include sodium, potassium and calcium salts of 5'-guanylic acid, inosinic acid, 5'-ribonucleotide, uridylic acid, adenylic acid, sodium, potassium and calcium salts thereof, and yeast extract, and the like. The content of such a nucleic acid seasoning is preferably between 0% and 0.2% by weight, more preferably between 0.005% and 0.2% by weight, and even more preferably between 0.01% and 0.1% by weight.

As a protein, water-soluble proteins such as gelatin may be used. Such proteins may be used singly or in combination of two or more types. The content of such a protein in the liquid seasoning of the present invention is between 0.1% and 2% by weight, and preferably between 0.2% and 1% by weight, based on the total weight, in terms of the improvement of soy sauce flavor such as an increase in salty taste or a decrease in the abnormal taste or bitter taste.

Examples of a protein hydrolysate may include a partial hydrolysate of gelatin and a soybean peptide. These substances may be used singly or in combination of two or more types. The content of such a protein hydrolysate in the liquid seasoning of the present invention is between 0.01% and 2% by weight, and preferably between 0.02% and 1% by weight, in terms of the improvement of soy sauce flavor, such as an increase in the salty taste or a decrease in the abnormal taste or bitter taste.

The liquid seasoning of the present invention preferably further contains a flavor improver (E) that is not considered as component (D). Examples of such a flavor improver may include an organic acid or a salt thereof, an inorganic acid salt, an inorganic ammonium salt, a sweetener, whey mineral, a starch hydrolysate, a plant extract, and polysaccharide. These substances may be used singly or in combination of two or more types. Herein, an inorganic ammonium salt contains nitrogen, but it is not considered as component (D).

Examples of an organic acid or a salt thereof may include phytic acid, citric acid, and organic acid with a valence of two or less or a salt thereof.

Examples of citrate may include monosodium citrate, disodium citrate, trisodium citrate, monopotassium citrate, dipotassium citrate, tripotassium citrate, calcium citrate, and isocitric acid or a salt thereof. These substances may be used singly or in combination of two or more types. The content of such citric acid in the liquid seasoning of the present invention is preferably between 0.5% and 2% by weight, and more preferably between 0.7% and 1.5% by weight, in terms of the improvement of soy sauce flavor, such as an increase in the salty taste or a decrease in the abnormal taste or bitter taste.

The content of phytic acid in the liquid seasoning of the present invention is preferably between 0.1% and 2% by weight, and more preferably between 0.2% and 1% by weight, based on the total weight, in terms of the improvement of soy sauce flavor such as an increase in the salty taste or a decrease in the abnormal taste or bitter taste.

Examples of organic acid with a valence of two or less or a salt thereof include lactic acid, fumaric acid, adipic acid, tartaric acid, succinic acid, malic acid, acetic acid, oxalic acid, gluconic acid, pantothenic acid, saturated aliphatic monocarboxylic acid, alkaline metal salts thereof such as sodium or potassium, and alkaline-earth metal salts thereof such as calcium. These substances may be used singly or in combination of two or more types. In addition, ascorbic acid may also be used as an organic acid having the same effect. Of these, lactic acid, succinic acid, and malic acid or a salt thereof are preferable. When considered as a free acid, the content of lactic acid in the liquid seasoning of the present invention is preferably between 0.9% and 3% by weight, more preferably between 1.3% and 3% by weight, and even more preferably between 1.5% and 2.5% by weight. In the case of succinic acid, it is preferably between 0.004% and 2% by weight, more preferably between 0.06% and 1.5% by weight, and even more preferably between 0.1% and 1% by weight. In the case of malic acid, it is preferably between 0.05% and 2% by weight, and more preferably between 0.1% and 1.5% by weight. The aforementioned content of each organic acid is preferable, in terms of the improvement of soy sauce flavor, such as an increase in the salty taste or a decrease in the abnormal taste or bitter taste. The content of saturated aliphatic monocarboxylic acid (containing 6 or more carbon atoms) in the liquid seasoning of the present invention is preferably between 1 and 100 ppm by weight, in terms of the improvement of soy sauce flavor, such as an increase in the salty taste or a decrease in the abnormal taste or bitter taste. In the case of other organic acids, the content thereof in the liquid seasoning of the present invention is preferably between 0.01% and 3% by weight, and more preferably between 0.02% and 2% by weight, in terms of the improvement of soy sauce flavor, such as an increase in the salty taste or a decrease in the abnormal taste or bitter taste.

Examples of an inorganic acid salt used herein include calcium chloride, magnesium chloride, sodium sulfate, ferrous sulfate, magnesium sulfate, and a potassium alum salt. These substances may be used singly or in combination of two or more types. The content of such an inorganic acid salt in the liquid seasoning of the present invention is preferably between 0.1% and 5% by weight, and more preferably between 0.2% and 2% by weight, based on the total weight, in terms of the improvement of soy sauce flavor, such as an increase in the salty taste or a decrease in the abnormal taste or bitter taste.

Other examples of an inorganic acid salt include alkaline metal salts of phosphoric acid and inorganic carbonates.

Examples of such alkaline metal salts of phosphoric acid include sodium dihydrogen phosphate, disodium hydrogen phosphate, trisodium phosphate, potassium dihydrogen phosphate, dipotassium hydrogen phosphate, tripotassium phosphate, sodium tripolyphosphate, potassium tripolyphosphate, sodium metaphosphate, and potassium metaphosphate. These substances may be used singly or in combination of two or more types. The content of such a substance in the liquid seasoning of the present invention is preferably between 0.01% and 2% by weight, and more preferably between 0.02% and 1% by weight, based on the total weight, in terms of the improvement of soy sauce flavor, such as an increase in the salty taste or a decrease in the abnormal taste or bitter taste.

Examples of inorganic carbonates include alkali metal salts of carbonic acid, such as sodium or potassium, magnesium carbonate, and sodium bicarbonate. These substances may be used singly or in combination of two or more types. The content of such inorganic carbonate in the liquid seasoning of the present invention is preferably between 0.01% and 2% by weight, and more preferably between 0.02% and 1% by weight, based on the total weight, in terms of the improvement of soy sauce flavor, such as an increase in the salty taste or a decrease in the abnormal taste or bitter taste.

Examples of a sweetener include fructose, glucose, sucrose, lactose, trehalose, a licorice extract, sugar alcohol (sorbitol, mannitol, maltitol, reduced palatinose, xylitol, etc.), sodium glycyrrhizinate, a stevia extract, artificial sweeteners such as saccharin sodium, aspartame, acesulfame potassium, or sucralose, and extract sweeteners such as a tamarind extract. These substances may be used singly or in combination of two or more types. The content of such a stevia extract, licorice extract, or sodium glycyrrhizinate in the liquid seasoning of the present invention is preferably between 0.0001% and 0.1% by weight, and more preferably between 0.0005% and 0.01% by weight, based on the total weight, in terms of the improvement of soy sauce flavor, such as an increase in the salty taste or a decrease in the abnormal taste or bitter taste. In the case of other sweeteners, the content thereof in the liquid seasoning of the present invention is preferably between 0.1% and 2% by weight, and more preferably between 0.2% and 1% by weight, based on the total weight, in terms of the improvement of soy sauce flavor, such as an increase in the salty taste or a decrease in the abnormal taste or bitter taste. Saccharin sodium and aspartame contain nitrogen in their molecules. However, such nitrogen is not considered as component (D).

The content of whey mineral in the liquid seasoning of the present invention is preferably between 0.1% and 5% by weight, and more preferably between 0.2% and 2% by weight, based on the total weight, in terms of the improvement of soy sauce flavor such as an increase in the salty taste or a decrease in the abnormal taste or bitter taste.

Examples of a starch hydrolysate include dextrin, acid dissolution starch, oxidizedstarch, and cyclodextrin. These substances may be used singly or in combination of two or more types. The content of such a starch hydrolysate in the liquid seasoning of the present invention is preferably between 0.01% and 2% by weight, and more preferably between 0.02% and 1% by weight, based on the total weight, in terms of the improvement of soy sauce flavor, such as an increase in the salty taste or a decrease in the abnormal taste or bitter taste.

Examples of a plant extract include a perilla extract and a pepper extract. These extracts may be used singly or in combination of two or more types. The content of a perilla extract in the liquid seasoning of the present invention is preferably between 0.01% and 5% by weight, and more preferably between 0.02% and 3% by weight, based on the total weight, in terms of the improvement of soy sauce flavor, such as an increase in the salty taste or a decrease in the abnormal taste or bitter taste. The content of a pepper extract in the liquid seasoning of the present invention is preferably between 0.01 and 5 ppm by weight, and more preferably between 0.02 and 1 ppm by weight, based on the total weight, in terms of the improvement of soy sauce flavor, such as an increase in the salty taste or a decrease in the abnormal taste or bitter taste.

Examples of polysaccharide include carrageenan and Cyamoposis gum. These substances may be used singly or in combination of two or more types. The content of such polysaccharide in the liquid seasoning of the present invention is preferably between 0.01% and 2% by weight, and more preferably between 0.02% and 1% by weight, based on the total weight, in terms of the improvement of soy sauce flavor, such as an increase in the salty taste or a decrease in the abnormal taste or bitter taste.

In addition, the pH of the liquid seasoning of the present invention is preferably between pH 3 and 6.5, more preferably between pH 4 and 6, and even more preferably between 4.5 and 5.5, in terms of prevention of deterioration of the flavor. Moreover, the liquid seasoning of the present invention preferably has specific values such as a chlorine content between 4% and 9% by weight and a solid content between 20% and 45% by weight.

Furthermore, as additives used for increasing the salty taste, calcium lactate also have certain effects. However, when the mixed soy sauce is then cooked by heating, the calcium lactate causes inconvenience such that the cooked food becomes hardened. Thus, it is not preferable to add these additives to soy sauce having functions as a general-purpose seasoning.

Further, other additives such as ethanol, Japanese sweet rice wine, fermented vinegar, or a sweetener may also be added to the liquid seasoning of the present invention, depending on preferences. Thus, the above liquid seasoning can be processed into various soy sauce processed food products such as seasoning soy sauce or mop sauce.

The liquid seasoning of the present invention exhibits the effect of significantly improving hypertension, when it is continuously ingested. Accordingly, it is possible to describe on a vessel containing the liquid seasoning of the present invention the following messages: "this is suitable for those who are worried about blood pressure," "this is suitable for those who have relatively high blood pressure," "this acts to decrease blood pressure," "this has effect to control blood pressure," etc.

EXAMPLES

The present invention will be described more in detail in the following examples. The examples are provided for illustrative purposes only, and are not intended to limit the scope of the invention.

Test Example 1

Preparation of Base Soy Sauce

A commercially available low salt soy sauce D (nitrogen concentration: 1.5% by weight; sodium concentration: 3.18% by weight (common salt concentration: 8.1% by weight); and potassium concentration: 0.38% by weight) was concentrated under reduced pressure. The concentrated soy sauce was finally adjusted with volatile water and common salts, resulting in a nitrogen concentration of 1.92% by weight, a sodium concentration of 3.34% by weight (a common salt concentration of 8.5% by weight), and a potassium concentration of 0.45% by weight, thereby producing a low salt soy sauce A. In addition, a commercially available low salt soy sauce C (nitrogen concentration: 1.4% by weight; sodium concentration: 3.18% by weight (common salt concentration: 8.1% by weight); and potassium concentration: 0.26% by weight) was concentrated under reduced pressure. The concentrated soy sauce was finally adjusted with volatile water and common salts, resulting in a nitrogen concentration of 2.0% by weight, a sodium concentration of 3.30% by weight (a common salt concentration of 8.4% by weight), and a potassium concentration of 0.33% by weight, thereby producing a low salt soy sauce B.

(1) Test Examples 1-1 to 1-25

The thus produced low salt soy sauces were used as base soy sauces. To each of these base soy sauces, potassium chloride, an acidulant, a nucleic acid seasoning, a food material having an antihypertensive effect, and the like, were added.

In addition, as food materials exhibiting an antihypertensive effect, polyphenol preparation A (which was obtained by extracting from green robusta coffee beans using hot water for 4 hours and treating the obtained extract with an adsorbent (activated carbon or clay) for concentration, followed by spray drying; caffeoylquinic acids: approximately 40% by weight), polyphenol preparation B (which was obtained by subjecting FH-1041 manufactured by T. Hasegawa Co., Ltd. to spray drying; caffeoylquinic acids: approximately 54% by weight), peptide A (Peptide Straight manufactured by Nippon Supplement, Inc.), and peptide B (Peptino manufactured by Nihon Shokuhin Kako Co., Ltd.) were added to the base soy sauces, so as to prepare liquid seasonings with compositions shown in Table 1.

(2) Measurement of Sodium Content

The content of sodium in the liquid seasoning was measured using an atomic absorption spectrophotometer (Hitachi Polarization Zeeman Atomic Absorption Spectrophotometer Z-6100). The content of common salt was obtained by converting the obtained value to a common salt content.

(3) Measurement of Potassium Content

The content of potassium in the liquid seasoning was measured in the same manner as that for the aforementioned sodium concentration.

(4) Measurement of Nitrogen Content

The concentration of nitrogen in the liquid seasoning was measured using a total nitrogen analyzer (Mitsubishi Chemical Corp. TN-05). In the table, the values of nitrogen contents in the liquid seasonings other than the food material having an antihypertensive effect (C) are shown.

(5) Sensory Evaluation Procedure

Ten panelists performed sensory evaluation on the obtained liquid seasoning (low salt soy sauces), in terms of its salty taste and bitter taste. Moreover, the soy sauces were also subjected to comprehensive evaluation, in which the general quality of soy sauce was evaluated. Evaluation standards are shown below. The obtained results are shown in Table 1.
[Evaluation Standards for Salty Taste]
1: The same level as that of low salt soy sauce (corresponding to 9% by weight of common salt)
2: An intermediate level between low salt soy sauce and regular soy sauce (common product) (corresponding to 14% by weight of common salt)
3: Slightly weaker than a regular product (common product)
4: The same level as that of a regular product (common product)
5: Stronger than a regular product (common product)
[Evaluation Standards for Bitter Taste]
1: None
2: Very slightly felt
3: Slightly felt
4: Felt
5: Strongly felt
[Evaluation Standards for Abnormal Taste]
1: None
2: Very slightly felt
3: Slightly felt
4: Felt
5: Strongly felt
[Criteria of Judgment in Comprehensive Evaluation]
E: It has a salty taste (4 or more), but does not have a bitter taste and abnormal taste (1 or less)
G: It has a salty taste (4 or more), and has a slight extent of a bitter taste and abnormal taste (2 or less)
M: It has a weak salty taste (1 or less) but does not have a bitter taste and abnormal taste (1 or less), or it has rather a weak salty taste (3 or less) and has a slight extent of a bitter taste and abnormal taste (3 or less)
P: It has a bitter taste and abnormal taste (3 or more)

TABLE 1

| | | Test Example 1 | | | | | | | | | | | | |
|---|---|---|---|---|---|---|---|---|---|---|---|---|---|
| | | 1-1 | 1-2 | 1-3 | 1-4 | 1-5 | 1-6 | 1-7 | 1-8 | 1-9 | 1-10 | 1-11 | 1-12 | 1-13 |
| Composition of seasoning (% by weight) | Low salt soy sauce A | 95.1 | 94.7 | 94.1 | 94.9 | 94.4 | 90.3 | 90.3 | | | | | | |
| | Low salt soy sauce B | | | | | | | | 95.7 | 95.1 | 92.5 | 93.8 | | |
| | Low salt soy sauce C | | | | | | | | | | | | 100 | |
| | Low salt soy sauce D | | | | | | | | | | | | | 100 |
| | Potassium chloride | 4 | 4 | 4 | 4 | 4 | 4 | 4 | 3 | 3 | 5 | 3 | | |
| | Lactic acid | 0.45 | 0.45 | 0.45 | 0.45 | 0.45 | 0.45 | 0.45 | 0.5 | 0.5 | 0.5 | 0.5 | | |
| | Citric acid | 0.05 | 0.05 | 0.05 | 0.05 | 0.05 | 0.05 | 0.05 | 0.04 | 0.04 | 0.04 | 0.04 | | |
| | Malic acid | 0.05 | 0.05 | 0.05 | 0.05 | 0.05 | 0.05 | 0.05 | 0.04 | 0.04 | 0.04 | 0.04 | | |
| | Disodium succinate | 0.08 | 0.08 | 0.08 | 0.08 | 0.08 | 0.08 | 0.08 | 0.06 | 0.06 | 0.06 | 0.06 | | |
| | Disodium inosinate | 0.04 | 0.04 | 0.04 | 0.04 | 0.04 | 0.04 | 0.04 | 0.05 | 0.05 | 0.05 | 0.05 | | |
| | Sodium aspartate monohydrate | | | | | | | | | | | | | |
| | Sodium glutamate monohydrate | | | | | | | | | | | | | |
| | Polyphenol preparation A | 0.25 | 0.63 | 1.25 | | | | | 0.63 | 1.25 | | | | |
| | Polyphenol preparation B | | | | 0.46 | 0.92 | | | | | 1.85 | | | |
| | Peptide A | | | | | | 5 | | | | | 2.5 | | |
| | Peptide B | | | | | | | 5 | | | | | | |
| Analytical value (% by weight) | Sodium concentration | 3.20 | 3.19 | 3.17 | 3.20 | 3.18 | 3.05 | 3.05 | 3.18 | 3.16 | 3.07 | 3.12 | 3.19 | 3.20 |
| | Common salt concentration | 8.15 | 8.12 | 8.07 | 8.13 | 8.09 | 7.75 | 7.75 | 8.10 | 8.04 | 7.82 | 7.94 | 8.11 | 8.13 |
| | Potassium concentration | 2.53 | 2.53 | 2.53 | 2.53 | 2.53 | 2.51 | 2.51 | 1.89 | 1.89 | 2.93 | 1.88 | 0.26 | 0.38 |
| | Nitrogen concentration in liquid seasoning excluding components (C) and (E) | 1.83 | 1.82 | 1.81 | 1.83 | 1.82 | 1.74 | 1.74 | 1.92 | 1.91 | 1.86 | 1.88 | 1.42 | 1.51 |
| | Acidic amino acid | 1.81 | 1.80 | 1.79 | 1.80 | 1.79 | 1.72 | 1.72 | 1.34 | 1.33 | 1.29 | 1.31 | 1.10 | 1.60 |
| | Free α-amino acid | 7.04 | 7.01 | 6.96 | 7.02 | 6.99 | 6.68 | 6.68 | 7.56 | 7.51 | 7.30 | 7.41 | 6.10 | 6.20 |
| | Aspartic acid | 0.68 | 0.68 | 0.68 | 0.68 | 0.68 | 0.65 | 0.65 | 0.12 | 0.12 | 0.12 | 0.12 | 0.10 | 0.60 |
| | Glutamic acid | 1.13 | 1.13 | 1.12 | 1.13 | 1.12 | 1.07 | 1.07 | 1.24 | 1.24 | 1.20 | 1.22 | 1.00 | 1.00 |
| Calculated value | Asp/K | 0.27 | 0.27 | 0.27 | 0.27 | 0.27 | 0.26 | 0.26 | 0.07 | 0.07 | 0.04 | 0.06 | 0.39 | 1.57 |
| | Asp/N | 0.37 | 0.37 | 0.37 | 0.37 | 0.37 | 0.37 | 0.37 | 0.06 | 0.06 | 0.06 | 0.06 | 0.07 | 0.40 |
| Evaluation | Salty taste | 4 | 4 | 4 | 4 | 4 | 4 | 4 | 4 | 4 | 4 | 4 | 1 | 1 |
| | Bitter taste | 1 | 1 | 1 | 1 | 1 | 2 | 2 | 1 | 1 | 1 | 1 | 1 | 1 |
| | Abnormal taste | 1 | 1 | 1 | 1 | 1 | 2 | 2 | 2 | 2 | 2 | 2 | 1 | 1 |
| | Comprehensive evaluation | E | E | E | E | E | G | G | G | G | G | G | M | M |

| | | Test Example 1 | | | | | | | | | | | |
|---|---|---|---|---|---|---|---|---|---|---|---|---|---|
| | | 1-14 | 1-15 | 1-16 | 1-17 | 1-18 | 1-19 | 1-20 | 1-21 | 1-22 | 1-23 | 1-24 | 1-25 |
| Composition of seasoning (% by weight) | Low salt soy sauce A | | | | | 95.3 | 94.3 | | | | | | |
| | Low salt soy sauce B | | | | | | | 96.3 | | | | | |
| | Low salt soy sauce C | 99.4 | 98.8 | | 95 | | | | 95.4 | 95.1 | | 98 | |
| | Low salt soy sauce D | | | 99.5 | | | | | | | 90 | | 95 |
| | Potassium chloride | | | | | 4 | 5 | 3 | 4 | 4 | 5 | 2 | 5 |
| | Lactic acid | | | | | 0.45 | 0.45 | 0.5 | | | | | |
| | Citric acid | | | | | 0.05 | 0.05 | 0.04 | | | | | |
| | Malic acid | | | | | 0.05 | 0.05 | 0.04 | | | | | |
| | Disodium succinate | | | | | 0.08 | 0.08 | 0.06 | | | | | |
| | Disodium inosinate | | | | | 0.04 | 0.04 | 0.05 | | | | | |
| | Sodium aspartate monohydrate | | | | | | | | | | | | |
| | Sodium glutamate monohydrate | | | | | | | | | | | | |
| | Polyphenol preparation A | 0.63 | 1.25 | | | | | | 0.63 | 0.92 | | | |
| | Polyphenol preparation B | | | 0.46 | | | | | | | 5 | | |
| | Peptide A | | | | 5 | | | | | | | | |
| | Peptide B | | | | | | | | | | | | |

TABLE 1-continued

| | | | | | | | | | | | | | |
|---|---|---|---|---|---|---|---|---|---|---|---|---|---|
| Analytical value (% by weight) | Sodium concentration | 3.17 | 3.15 | 3.18 | 3.03 | 3.21 | 3.18 | 3.20 | 3.04 | 3.03 | 2.88 | 3.12 | 3.03 |
| | Common salt concentration | 8.06 | 8.01 | 8.09 | 7.70 | 8.17 | 8.09 | 8.15 | 7.73 | 7.71 | 7.32 | 7.95 | 7.72 |
| | Potassium concentration | 0.25 | 0.25 | 0.38 | 0.24 | 2.53 | 3.05 | 1.89 | 2.34 | 2.34 | 2.97 | 1.30 | 2.98 |
| | Nitrogen concentration in liquid seasoning excluding components (C) and (E) | 1.41 | 1.40 | 1.50 | 1.35 | 1.84 | 1.82 | 1.93 | 1.35 | 1.35 | 1.36 | 1.39 | 1.43 |
| | Acidic amino acid | 1.09 | 1.09 | 1.59 | 1.05 | 1.81 | 1.79 | 1.35 | 1.05 | 1.05 | 1.44 | 1.08 | 1.52 |
| | Free α-amino acid | 6.06 | 6.02 | 6.17 | 5.80 | 7.05 | 6.98 | 7.61 | 5.82 | 5.80 | 5.58 | 5.98 | 5.89 |
| | Aspartic acid | 0.10 | 0.10 | 0.60 | 0.10 | 0.69 | 0.68 | 0.13 | 0.10 | 0.10 | 0.54 | 0.10 | 0.57 |
| | Glutamic acid | 0.99 | 0.99 | 1.00 | 0.95 | 1.13 | 1.12 | 1.25 | 0.95 | 0.95 | 0.90 | 0.98 | 0.95 |
| Calculated value | Asp/K | 0.39 | 0.39 | 1.57 | 0.39 | 0.27 | 0.22 | 0.07 | 0.04 | 0.04 | 0.18 | 0.08 | 0.19 |
| | Asp/N | 0.07 | 0.07 | 0.40 | 0.07 | 0.37 | 0.37 | 0.06 | 0.07 | 0.07 | 0.40 | 0.07 | 0.40 |
| Evaluation | Salty taste | 1 | 1 | 1 | 1 | 4 | 4 | 4 | 3 | 3 | 3 | 2 | 3 |
| | Bitter taste | 1 | 1 | 1 | 4 | 1 | 1 | 1 | 2 | 2 | 3 | 2 | 3 |
| | Abnormal taste | 1 | 1 | 1 | 4 | 1 | 1 | 1 | 1 | 1 | 3 | 1 | 1 |
| | Comprehensive evaluation | M | M | M | P | E | E | E | M | M | P | M | M |

(6) Assay of Antihypertensive Effect

Test Example 2

(a) Animals to be Used

Male spontaneous hypertensive rats (SHR) with an age of 16 weeks old were fed under conditions consisting of a room temperature of 25±1° C., a humidity of 55±10% RH, and a lighting period of 12 hours (from 7 o'clock in the morning to 7 o'clock in the evening) (in a rat breeding room).

(b) Administration and Dosage

A normal saline solution was administered to a control group. Administration was carried out via an oral administration route. Using a metallic feeding tube, the liquid seasoning was compulsively administered to the rats. The dosage thereof was set at 5 ml/kg.

(c) Assay Procedure

A group consisting of 3 fasting rats (SHR) was used. The systolic blood pressure of the caudal artery thereof was measured, before and 6 hours after the oral administration of the liquid seasoning, using a commercially available noninvasive blood pressure measuring device used for rats (manufactured by Softron).

(d) Statistical Processing

The obtained measurement results were expressed with the mean value of a changed rate and a standard error (SE), and Student's T-test was then carried out.

In Table 1, the antihypertensive effect of each of Test Examples 1-2, 1-3, 1-6, 1-12, 1-14, 1-15, 1-17 and 1-18, and a normal saline solution, was analyzed. The results are shown in FIG. 1.

Test Example 3

(a) Animals to be Used

Male spontaneous hypertensive rats (SHR) with an age of 5 weeks old were fed under conditions consisting of a room temperature of 25±1° C., a humidity of 55±10% RH, and a lighting period of 12 hours (from 7 o'clock in the morning to 7 o'clock in the evening) (in a rat breeding room).

(b) Administration and Dosage

Administration was carried out via an oral administration route. Using a metallic feeding tube, the liquid seasoning was compulsively administered to the rats once a day. The dosage thereof was set at 5 ml/kg.

(c) Assay Procedure

A group consisting of 6 SHR rats (with an age of 6 weeks old when the test was initiated) was used. The systolic blood pressure of the caudal artery thereof was measured, once a week, over 6 weeks, using a commercially available noninvasive blood pressure measuring device used for rats (manufactured by Softron).

(d) Statistical Processing

The obtained measurement results were expressed with the mean value of a changed rate and a standard error (SE), and Student's T-test was then carried out.

In Table 1, the antihypertensive effect of each of Test Examples 1-4, 1-12, and 1-18 was analyzed. The results are shown in FIG. 2.

Figure 2:
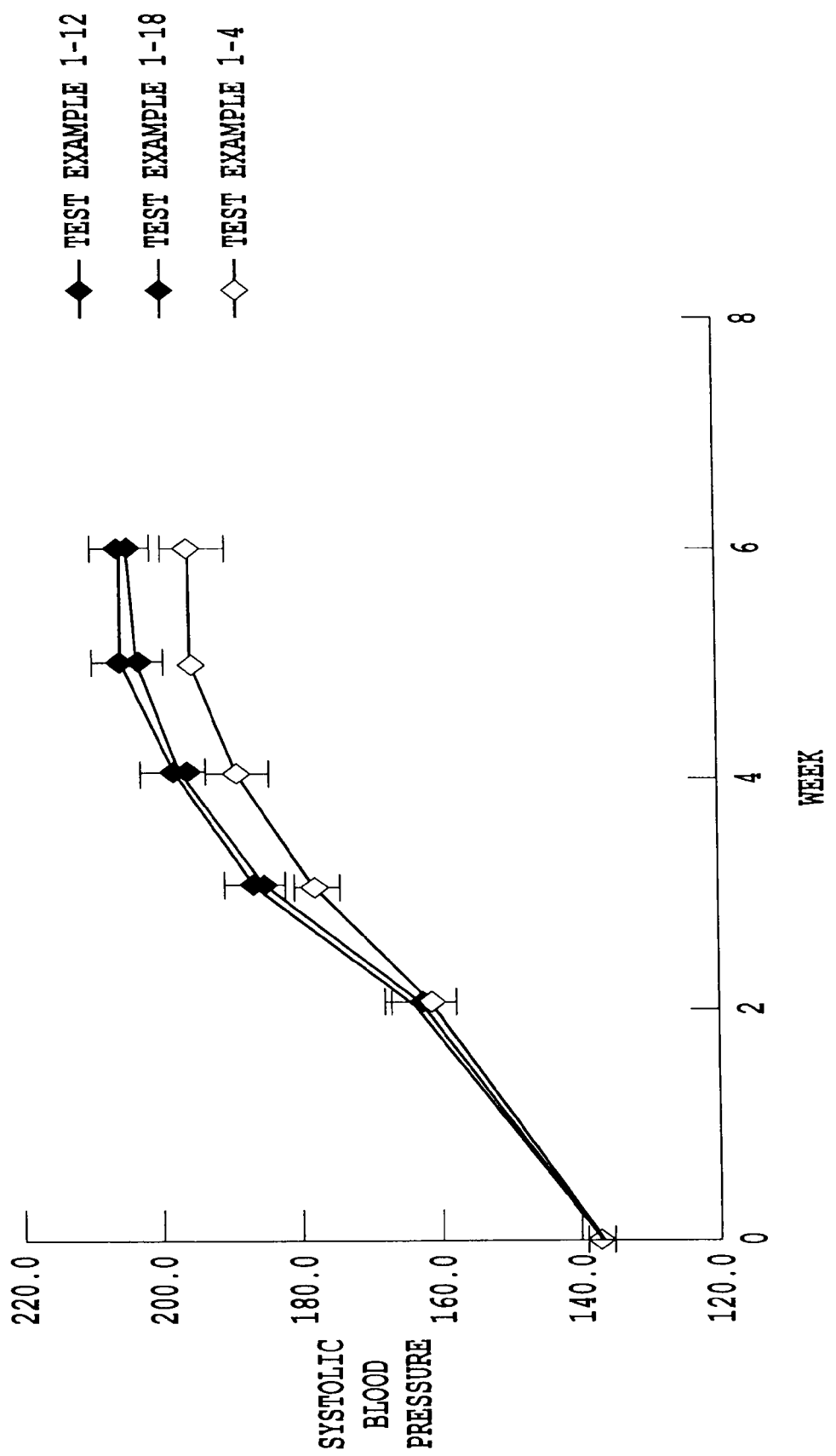
FIG. 2 shows a change in the rat systolic blood pressure due to a continuous ingestion of the liquid seasoning of the present invention.

As is apparent from FIGS. 1 and 2, it was found that the blood pressure is decreased by the ingestion of the liquid seasoning of the present invention, and that an increase in the blood pressure was suppressed by continuous ingestion thereof. (In FIGS. 1 and 2, the liquid seasonings of Test Examples 1-12 and 1-18 contain no food products having an antihypertensive effect.) Moreover, as is clear from Table 1, it was found that even in the case of a liquid seasoning, which has a low common salt concentration and to which a food material having an antihypertensive effect is mixed, the liquid seasoning is able to have a sufficient salty taste by adjusting the potassium content to the range in the invention of the present application and by using nitrogen contained at 1.6% by weight or more in the liquid seasoning excluding component (C), and thus the liquid seasoning has a taste level sufficiently good for continual ingestion as soy sauce.

Test Examples 4 to 7

Preparation of Base Soy Sauce

A commercially available low salt soy sauce E (sodium concentration: 3.19% by weight (common salt concentration:

8.11% by weight); nitrogen concentration: 1.51% by weight; and potassium concentration: 0.38% by weight) was used. In addition, the low salt soy sauce E was concentrated under reduced pressure. The concentrated soy sauce was finally adjusted with volatile water and common salts, resulting in a sodium concentration of 3.34% by weight (common salt concentration of 8.5% by weight), a nitrogen concentration of 1.80% by weight, and a potassium concentration of 0.45% by weight, thereby producing a low salt soy sauce F. Moreover, a commercially available low salt soy sauce G (sodium concentration: 3.19% by weight (common salt concentration: 8.11% by weight); nitrogen concentration: 1.42% by weight; and potassium concentration: 0.26% by weight) was used to measure the antihypertensive effect.

(1) Test Examples 4-1 to 4-20

The aforementioned low salt soy sauces E and F were used as base soy sauces. To each of these base soy sauces, potassium chloride, a flavor improver, a food material having an antihypertensive effect, an amino acid seasoning, and the like, were added, so as to prepare liquid seasonings with compositions shown in Table 2. Analysis of each component and sensory evaluation were carried out in the same manner as in Test Example 1. The results are shown in Table 2.

TABLE 2

|  |  | Test Example 4 Comparative example | | | | | | | | | |
|---|---|---|---|---|---|---|---|---|---|---|---|
|  |  | 4-1 | 4-2 | 4-3 | 4-4 | 4-5 | 4-6 | 4-7 | 4-8 | 4-9 | 4-10 |
| Composition of seasoning (% by weight) | Low salt soy sauce E | 100 |  | 96 | 95.9 | 95.5 | 93.9 |  |  |  |  |
|  | Low salt soy sauce F |  | 100 |  |  |  |  | 95.4 | 94.75 | 95.5 | 93.5 |
|  | Potassium chloride |  |  | 4 | 4 | 4 | 4 | 4 | 4 | 4 | 4 |
|  | Disodium succinate |  |  |  | 0.1 |  | 0.1 | 0.1 |  |  |  |
|  | Lactic acid |  |  |  |  | 0.5 | 0.5 | 0.5 |  |  |  |
|  | Chlorogenic acid preparation |  |  |  |  |  |  |  | 1.25 |  |  |
|  | γ-aminobutyric acid |  |  |  |  |  |  |  |  | 0.5 |  |
|  | Peptide preparation |  |  |  |  |  |  |  |  |  | 2.5 |
|  | Sodium aspartate monohydrate |  |  |  |  |  | 1 |  |  |  |  |
|  | Sodium glutamate monohydrate |  |  |  |  |  | 0.5 |  |  |  |  |
| Analytical value (% by weight) | Sodium concentration | 3.19 | 3.34 | 3.06 | 3.09 | 3.05 | 3.21 | 3.21 | 3.16 | 3.19 | 3.12 |
|  | Common salt concentration | 8.11 | 8.50 | 7.79 | 7.85 | 7.75 | 8.18 | 8.18 | 8.05 | 8.12 | 7.95 |
|  | Potassium concentration | 0.38 | 0.45 | 2.46 | 2.46 | 2.46 | 2.45 | 2.53 | 2.52 | 2.53 | 2.52 |
|  | Nitrogen concentration excluding nitrogen from (C) and (E) | 1.51 | 1.80 | 1.45 | 1.45 | 1.44 | 1.54 | 1.72 | 1.71 | 1.72 | 1.68 |
|  | Glutamic acid concentration | 1.00 | 1.20 | 0.96 | 0.96 | 0.96 | 1.33 | 1.14 | 1.14 | 1.15 | 1.12 |
|  | Aspartic acid concentration | 0.60 | 0.70 | 0.58 | 0.58 | 0.57 | 1.33 | 0.67 | 0.66 | 0.67 | 0.65 |
|  | Acidic amino acid concentration | 1.60 | 1.90 | 1.54 | 1.53 | 1.53 | 2.66 | 1.81 | 1.80 | 1.81 | 1.78 |
|  | Basic amino acid concentration | 0.80 | 1.00 | 0.77 | 0.77 | 0.76 | 0.75 | 0.95 | 0.95 | 0.96 | 0.94 |
|  | Free amino acid concentration | 6.20 | 7.40 | 5.95 | 5.95 | 5.92 | 6.98 | 7.06 | 7.01 | 7.07 | 6.92 |
| Calculated value | Asp/K | 1.58 | 1.56 | 0.23 | 0.23 | 0.23 | 0.54 | 0.26 | 0.26 | 0.26 | 0.26 |
|  | Asp/N | 0.40 | 0.39 | 0.40 | 0.40 | 0.40 | 0.87 | 0.39 | 0.39 | 0.39 | 0.39 |
| Evaluation | Salty taste | 1 | 1 | 3 | 3 | 3 | 4 | 4 | 3 | 3 | 3 |
|  | Bitter taste | 1 | 1 | 3 | 2 | 2 | 1 | 1 | 2 | 2 | 2 |
|  | Abnormal taste | 1 | 1 | 1 | 1 | 1 | 1 | 1 | 2 | 2 | 2 |
|  | Comprehensive evaluation | M | M | M | M | M | E | E | M | M | M |

|  |  | Test Examples 4 Examples of the present invention | | | | | | | | | |
|---|---|---|---|---|---|---|---|---|---|---|---|
|  |  | 4-11 | 4-12 | 4-13 | 4-14 | 4-15 | 4-16 | 4-17 | 4-18 | 4-19 | 4-20 |
| Composition of seasoning (% by weight) | Low salt soy sauce E | 93.15 | 93.9 | 91.9 |  |  |  | 92.55 | 91.3 | 93.3 | 91.3 |
|  | Low salt soy sauce F |  |  |  | 94.15 | 94.9 | 92.9 |  |  |  |  |
|  | Potassium chloride | 4 | 4 | 4 | 4 | 4 | 4 | 4 | 4 | 4 | 4 |
|  | Disodium succinate | 0.1 | 0.1 | 0.1 | 0.1 | 0.1 | 0.1 | 0.2 | 0.2 | 0.2 | 0.2 |
|  | Lactic acid |  |  |  | 0.5 | 0.5 | 0.5 | 0.5 | 0.5 | 0.5 | 0.5 |
|  | Chlorogenic acid preparation | 1.25 |  |  | 1.25 |  |  | 1.25 | 2.5 |  |  |
|  | γ-aminobutyric acid |  | 0.5 |  |  | 0.5 |  |  |  | 0.5 |  |
|  | Peptide preparation |  |  | 2.5 |  |  | 2.5 |  |  |  | 2.5 |
|  | Sodium aspartate monohydrate | 1 | 1 | 1 |  |  |  | 1 | 1 | 1 | 1 |
|  | Sodium glutamate monohydrate | 0.5 | 0.5 | 0.5 |  |  |  | 0.5 | 0.5 | 0.5 | 0.5 |
| Analytical value (% by weight) | Sodium concentration | 3.19 | 3.21 | 3.15 | 3.17 | 3.20 | 3.13 | 3.20 | 3.16 | 3.22 | 3.16 |
|  | Common salt concentration | 8.12 | 8.18 | 8.02 | 8.07 | 8.14 | 7.97 | 8.14 | 8.04 | 8.20 | 8.04 |
|  | Potassium concentration | 2.45 | 2.45 | 2.45 | 2.52 | 2.52 | 2.52 | 2.45 | 2.44 | 2.45 | 2.44 |
|  | Nitrogen concentration excluding nitrogen from (C) and (E) | 1.52 | 1.54 | 1.51 | 1.69 | 1.71 | 1.67 | 1.52 | 1.50 | 1.53 | 1.50 |
|  | Glutamic acid concentration | 1.32 | 1.33 | 1.31 | 1.13 | 1.14 | 1.11 | 1.32 | 1.31 | 1.33 | 1.31 |
|  | Aspartic acid concentration | 1.33 | 1.33 | 1.32 | 0.66 | 0.66 | 0.65 | 1.32 | 1.32 | 1.33 | 1.32 |
|  | Acidic amino acid concentration | 2.65 | 2.66 | 2.63 | 1.79 | 1.80 | 1.77 | 2.64 | 2.62 | 2.65 | 2.62 |
|  | Basic amino acid concentration | 0.75 | 0.75 | 0.74 | 0.94 | 0.95 | 0.93 | 0.74 | 0.73 | 0.75 | 0.73 |
|  | Free amino acid concentration | 6.94 | 6.98 | 6.86 | 6.97 | 7.02 | 6.87 | 6.90 | 6.82 | 6.95 | 6.82 |
| Calculated value | Asp/K | 0.54 | 0.54 | 0.54 | 0.26 | 0.26 | 0.26 | 0.54 | 0.54 | 0.54 | 0.54 |
|  | Asp/N | 0.87 | 0.87 | 0.88 | 0.39 | 0.39 | 0.39 | 0.87 | 0.88 | 0.87 | 0.88 |
| Evaluation | Salty taste | 4 | 4 | 4 | 4 | 4 | 4 | 4 | 4 | 4 | 4 |
|  | Bitter taste | 1 | 1 | 1 | 1 | 1 | 1 | 1 | 1 | 1 | 1 |

TABLE 2-continued

| | | | | | | | | | | |
|---|---|---|---|---|---|---|---|---|---|---|
| Abnormal taste | 1 | 1 | 2 | 1 | 1 | 2 | 1 | 1 | 1 | 2 |
| Comprehensive evaluation | E | E | G | E | E | G | E | E | E | G |

(2) Test Examples 5-1 to 5-19

The aforementioned low salt soy sauce E was used as the base soy sauce. Potassium chloride, a flavor improver, a food material having an antihypertensive effect, an amino acid seasoning, and the like, were added thereto, so as to prepare liquid seasonings with compositions shown in Table 3. Analysis of each component and sensory evaluation were carried out in the same manner as in Test Example 1. The results are shown in Table 3.

TABLE 3

| | | Test Example 5 Examples of the present invention | | | | | | | | | |
|---|---|---|---|---|---|---|---|---|---|---|---|
| | | 5-1 | 5-2 | 5-3 | 5-4 | 5-5 | 5-6 | 5-7 | 5-8 | 5-9 | 5-10 |
| Composition of seasoning (% by weight) | Low salt soy sauce E | 93.05 | 93.05 | 93.05 | 92.25 | 92.25 | 92.25 | 92.25 | 92.25 | 92.25 | 92.25 |
| | Potassium chloride | 4 | 4 | 4 | 4 | 4 | 4 | 4 | 4 | 4 | 4 |
| | Succinic acid | 0.2 | | | | | | | | | |
| | Ascorbic acid | | 0.2 | | | | | | | | |
| | Malic acid | | | 0.2 | | | | | | | |
| | Sodium lactate | | | | 1.0 | | | | | | |
| | Disodium succinate | | | | | 1.0 | | | | | |
| | Sodium ascorbate | | | | | | 1.0 | | | | |
| | Calcium pantothenate | | | | | | | 1.0 | | | |
| | Sodium dihydrogen phosphate | | | | | | | | 1.0 | | |
| | Sodium carbonate | | | | | | | | | 1.0 | |
| | Ammonium chloride | | | | | | | | | | 1.0 |
| | Sucrose | | | | | | | | | | |
| | Saccharin sodium | | | | | | | | | | |
| | Aspartame | | | | | | | | | | |
| | Partial hydrolysate of gelatin | | | | | | | | | | |
| | Soybean peptide | | | | | | | | | | |
| | Perilla extract | | | | | | | | | | |
| | Capsaicin | | | | | | | | | | |
| | Carrageenan | | | | | | | | | | |
| | Cyamoposis gum | | | | | | | | | | |
| | Chlorogenic acid preparation | 1.25 | 1.25 | 1.25 | 1.25 | 1.25 | 1.25 | 1.25 | 1.25 | 1.25 | 1.25 |
| | Sodium aspartate monohydrate | 1 | 1 | 1 | 1 | 1 | 1 | 1 | 1 | 1 | 1 |
| | Sodium glutamate monohydrate | 0.5 | 0.5 | 0.5 | 0.5 | 0.5 | 0.5 | 0.5 | 0.5 | 0.5 | 0.5 |
| Analytical value (% by weight) | Sodium concentration | 3.21 | 3.16 | 3.16 | 3.14 | 3.14 | 3.14 | 3.14 | 3.14 | 3.14 | 3.14 |
| | Common salt concentration | 8.18 | 8.04 | 8.04 | 7.98 | 7.98 | 7.98 | 7.98 | 7.98 | 7.98 | 7.98 |
| | Potassium concentration | 2.45 | 2.45 | 2.45 | 2.45 | 2.45 | 2.45 | 2.45 | 2.45 | 2.45 | 2.45 |
| | Nitrogen concentration excluding nitrogen from (C) and (E) | 1.52 | 1.52 | 1.52 | 1.51 | 1.51 | 1.51 | 1.51 | 1.51 | 1.51 | 1.51 |
| | Glutamic acid concentration | 1.32 | 1.32 | 1.32 | 1.32 | 1.32 | 1.32 | 1.32 | 1.32 | 1.32 | 1.32 |
| | Aspartic acid concentration | 1.33 | 1.33 | 1.33 | 1.32 | 1.32 | 1.32 | 1.32 | 1.32 | 1.32 | 1.32 |
| | Acidic amino acid concentration | 2.65 | 2.65 | 2.65 | 2.64 | 2.64 | 2.64 | 2.64 | 2.64 | 2.64 | 2.64 |
| | Basic amino acid concentration | 0.74 | 0.74 | 0.74 | 0.74 | 0.74 | 0.74 | 0.74 | 0.74 | 0.74 | 0.74 |
| | Free amino acid concentration | 6.93 | 6.93 | 6.93 | 6.88 | 6.88 | 6.88 | 6.88 | 6.88 | 6.88 | 6.88 |
| Calculated value | Asp/K | 0.54 | 0.54 | 0.54 | 0.54 | 0.54 | 0.54 | 0.54 | 0.54 | 0.54 | 0.54 |
| | Asp/N | 0.87 | 0.87 | 0.87 | 0.88 | 0.88 | 0.88 | 0.88 | 0.88 | 0.88 | 0.88 |
| Evaluation | Salty taste | 4 | 4 | 4 | 4 | 4 | 4 | 4 | 4 | 4 | 4 |
| | Bitter taste | 1 | 1 | 1 | 1 | 1 | 1 | 1 | 1 | 1 | 1 |
| | Abnormal taste | 1 | 1 | 1 | 1 | 1 | 1 | 1 | 1 | 1 | 1 |
| | Comprehensive evaluation | E | E | E | E | E | E | E | E | E | E |

| | | Test Example 5 Examples of the present invention | | | | | | | | |
|---|---|---|---|---|---|---|---|---|---|---|
| | | 5-11 | 5-12 | 5-13 | 5-14 | 5-15 | 5-16 | 5-17 | 5-18 | 5-19 |
| Composition of seasoning (% by weight) | Low salt soy sauce E | 92.75 | 92.75 | 92.75 | 92.75 | 92.75 | 92.25 | 93.24 | 92.75 | 92.75 |
| | Potassium chloride | 4 | 4 | 4 | 4 | 4 | 4 | | 4 | 4 |
| | Succinic acid | | | | | | | | | |
| | Ascorbic acid | | | | | | | | | |
| | Malic acid | | | | | | | | | |
| | Sodium lactate | | | | | | | | | |
| | Disodium succinate | | | | | | | | | |
| | Sodium ascorbate | | | | | | | | | |
| | Calcium pantothenate | | | | | | | | | |
| | Sodium dihydrogen phosphate | | | | | | | | | |
| | Sodium carbonate | | | | | | | | | |
| | Ammonium chloride | | | | | | | | | |
| | Sucrose | 0.5 | | | | | | | | |
| | Saccharin sodium | | 0.5 | | | | | | | |

TABLE 3-continued

|  |  |  |  |  |  |  |  |  |  |
|---|---|---|---|---|---|---|---|---|---|
|  | Aspartame |  |  | 0.5 |  |  |  |  |  |
|  | Partial hydrolysate of gelatin |  |  |  | 0.5 |  |  |  |  |
|  | Soybean peptide |  |  |  |  | 0.5 |  |  |  |
|  | Perilla extract |  |  |  |  |  | 1.0 |  |  |
|  | Capsaicin |  |  |  |  |  |  | 0.00005 |  |
|  | Carrageenan |  |  |  |  |  |  |  | 0.5 |
|  | Cyamoposis gum |  |  |  |  |  |  |  |  | 0.5 |
|  | Chlorogenic acid preparation | 1.25 | 1.25 | 1.25 | 1.25 | 1.25 | 1.25 | 1.25 | 1.25 | 1.25 |
|  | Sodium aspartate monohydrate | 1 | 1 | 1 | 1 | 1 | 1 | 1 | 1 | 1 |
|  | Sodium glutamate monohydrate | 0.5 | 0.5 | 0.5 | 0.5 | 0.5 | 0.5 | 0.5 | 0.5 | 0.5 |
| Analytical value (% by weight) | Sodium concentration | 3.15 | 3.15 | 3.15 | 3.15 | 3.15 | 3.14 | 3.17 | 3.15 | 3.15 |
|  | Common salt concentration | 8.02 | 8.02 | 8.02 | 8.02 | 8.02 | 7.98 | 8.06 | 8.02 | 8.02 |
|  | Potassium concentration | 2.45 | 2.45 | 2.45 | 2.45 | 2.45 | 2.45 | 2.45 | 2.45 | 2.45 |
|  | Nitrogen concentration excluding nitrogen from (C) and (E) | 1.52 | 1.52 | 1.52 | 1.52 | 1.52 | 1.51 | 1.53 | 1.52 | 1.52 |
|  | Glutamic acid concentration | 1.32 | 1.32 | 1.32 | 1.32 | 1.32 | 1.32 | 1.33 | 1.32 | 1.32 |
|  | Aspartic acid concentration | 1.33 | 1.33 | 1.33 | 1.33 | 1.33 | 1.32 | 1.33 | 1.33 | 1.33 |
|  | Acidic amino acid concentration | 2.65 | 2.65 | 2.65 | 2.65 | 2.65 | 2.64 | 2.65 | 2.65 | 2.65 |
|  | Basic amino acid concentration | 0.74 | 0.74 | 0.74 | 0.74 | 0.74 | 0.74 | 0.75 | 0.74 | 0.74 |
|  | Free amino acid concentration | 6.91 | 6.91 | 6.91 | 6.91 | 6.91 | 6.88 | 6.94 | 6.91 | 6.91 |
| Calculated value | Asp/K | 0.54 | 0.54 | 0.54 | 0.54 | 0.54 | 0.54 | 0.54 | 0.54 | 0.54 |
|  | Asp/N | 0.87 | 0.87 | 0.87 | 0.87 | 0.87 | 0.88 | 0.87 | 0.87 | 0.87 |
| Evaluation | Salty taste | 4 | 4 | 4 | 4 | 4 | 4 | 4 | 4 | 4 |
|  | Bitter taste | 1 | 1 | 1 | 1 | 1 | 1 | 1 | 1 | 1 |
|  | Abnormal taste | 1 | 1 | 1 | 1 | 1 | 1 | 1 | 1 | 1 |
|  | Comprehensive evaluation | E | E | E | E | E | E | E | E | E |

Test Example 6

(3) Test Examples 6-1 to 6-20

The aforementioned low salt soy sauces E and F were used as base soy sauces. Potassium chloride, a flavor improver, a food material having an antihypertensive effect, an amino acid seasoning, and the like, were added thereto, so as to prepare liquid seasonings with compositions shown in Table 4. Analysis of each component and sensory evaluation were carried out in the same manner as in Test Example 1. The results are shown in Table 4.

TABLE 4

|  |  | Test Example 6 Comparative example | | | | | | | | | |
|---|---|---|---|---|---|---|---|---|---|---|---|
|  |  | 6-1 | 6-2 | 6-3 | 6-4 | 6-5 | 6-6 | 6-7 | 6-8 | 6-9 | 6-10 |
| Composition of seasoning (% by weight) | Low salt soy sauce E | 100 |  | 96 | 95.95 | 95.8 | 92.55 |  |  |  |  |
|  | Low salt soy sauce F |  | 100 |  |  |  |  | 95.75 | 94.75 | 95.5 | 93.5 |
|  | Potassium chloride |  |  | 4 | 4 | 4 | 4 | 4 | 4 | 4 | 4 |
|  | Disodium inosinate |  |  |  | 0.05 |  | 0.05 | 0.05 |  |  |  |
|  | Citric acid |  |  |  |  | 0.2 | 0.2 | 0.2 |  |  |  |
|  | Chlorogenic acid preparation |  |  |  |  |  |  |  | 1.25 |  |  |
|  | γ-aminobutyric acid |  |  |  |  |  |  |  |  | 0.5 |  |
|  | Peptide preparation |  |  |  |  |  |  |  |  |  | 2.5 |
|  | Sodium aspartate monohydrate |  |  |  |  |  | 2 |  |  |  |  |
|  | Sodium glutamate monohydrate |  |  |  |  |  | 1.2 |  |  |  |  |
| Analytical value (% by weight) | Sodium concentration | 3.19 | 3.34 | 3.06 | 3.07 | 3.05 | 3.38 | 3.21 | 3.16 | 3.19 | 3.12 |
|  | Common salt concentration | 8.11 | 8.50 | 7.79 | 7.82 | 7.77 | 8.59 | 8.17 | 8.05 | 8.12 | 7.95 |
|  | Potassium concentration | 0.38 | 0.45 | 2.46 | 2.46 | 2.46 | 2.45 | 2.53 | 2.52 | 2.53 | 2.52 |
|  | Nitrogen concentration excluding nitrogen from (C) and (E) | 1.51 | 1.80 | 1.45 | 1.45 | 1.45 | 1.65 | 1.72 | 1.71 | 1.72 | 1.68 |
|  | Glutamic acid concentration | 1.00 | 1.20 | 0.96 | 0.96 | 0.96 | 1.87 | 1.15 | 1.14 | 1.15 | 1.12 |
|  | Aspartic acid concentration | 0.60 | 0.70 | 0.58 | 0.58 | 0.57 | 2.09 | 0.67 | 0.66 | 0.67 | 0.65 |
|  | Acidic amino acid concentration | 1.60 | 1.90 | 1.54 | 1.54 | 1.53 | 3.96 | 1.82 | 1.80 | 1.81 | 1.78 |
|  | Basic amino acid concentration | 0.80 | 1.00 | 0.77 | 0.77 | 0.77 | 0.74 | 0.96 | 0.95 | 0.96 | 0.94 |
|  | Free amino acid concentration | 6.20 | 7.40 | 5.95 | 5.95 | 5.94 | 8.22 | 7.09 | 7.01 | 7.07 | 6.92 |
| Calculated value | Asp/K | 1.58 | 1.56 | 0.23 | 0.23 | 0.23 | 0.85 | 0.27 | 0.26 | 0.26 | 0.26 |
|  | Asp/N | 0.40 | 0.39 | 0.40 | 0.40 | 0.40 | 1.27 | 0.39 | 0.39 | 0.39 | 0.39 |
| Evaluation | Salty taste | 1 | 1 | 3 | 3 | 3 | 4 | 4 | 3 | 3 | 3 |
|  | Bitter taste | 1 | 1 | 3 | 2 | 2 | 1 | 1 | 2 | 2 | 2 |
|  | Abnormal taste | 1 | 1 | 1 | 1 | 1 | 1 | 1 | 2 | 2 | 2 |
|  | Comprehensive evaluation | M | M | M | M | M | E | E | M | M | M |

TABLE 4-continued

|  |  | Test Example 6 Examples of the present invention ||||||||||
|---|---|---|---|---|---|---|---|---|---|---|---|
|  |  | 6-11 | 6-12 | 6-13 | 6-14 | 6-15 | 6-16 | 6-17 | 6-18 | 6-19 | 6-20 |
| Composition of seasoning (% by weight) | Low salt soy sauce E | 91.5 | 92.25 | 90.25 |  |  |  | 91.25 | 90 | 92 | 90 |
|  | Low salt soy sauce F |  |  |  | 94.5 | 95.25 | 93.25 |  |  |  |  |
|  | Potassium chloride | 4 | 4 | 4 | 4 | 4 | 4 | 4 | 4 | 4 | 4 |
|  | Disodium inosinate | 0.05 | 0.05 | 0.05 | 0.05 | 0.05 | 0.05 | 0.1 | 0.1 | 0.1 | 0.1 |
|  | Citric acid |  |  |  | 0.2 | 0.2 | 0.2 | 0.2 | 0.2 | 0.2 | 0.2 |
|  | Chlorogenic acid preparation | 1.25 |  |  | 1.25 |  |  | 1.25 | 2.5 |  |  |
|  | γ-aminobutyric acid |  | 0.5 |  |  | 0.5 |  |  |  | 0.5 |  |
|  | Peptide preparation |  |  | 2.5 |  |  | 2.5 |  |  |  | 2.5 |
|  | Sodium aspartate monohydrate | 2 | 2 | 2 |  |  |  | 2 | 2 | 2 | 2 |
|  | Sodium glutamate monohydrate | 1.2 | 1.2 | 1.2 |  |  |  | 1.2 | 1.2 | 1.2 | 1.2 |
| Analytical value (% by weight) | Sodium concentration | 3.34 | 3.37 | 3.31 | 3.17 | 3.20 | 3.13 | 3.35 | 3.31 | 3.37 | 3.31 |
|  | Common salt concentration | 8.51 | 8.57 | 8.41 | 8.07 | 8.13 | 7.96 | 8.52 | 8.42 | 8.58 | 8.42 |
|  | Potassium concentration | 2.45 | 2.45 | 2.44 | 2.52 | 2.53 | 2.52 | 2.44 | 2.44 | 2.45 | 2.44 |
|  | Nitrogen concentration excluding nitrogen from (C) and (E) | 1.63 | 1.64 | 1.61 | 1.70 | 1.71 | 1.68 | 1.63 | 1.61 | 1.64 | 1.61 |
|  | Glutamic acid concentration | 1.86 | 1.87 | 1.85 | 1.13 | 1.14 | 1.12 | 1.86 | 1.84 | 1.86 | 1.84 |
|  | Aspartic acid concentration | 2.09 | 2.09 | 2.08 | 0.66 | 0.67 | 0.65 | 2.09 | 2.08 | 2.09 | 2.08 |
|  | Acidic amino acid concentration | 3.95 | 3.96 | 3.93 | 1.80 | 1.81 | 1.77 | 3.94 | 3.92 | 3.95 | 3.92 |
|  | Basic amino acid concentration | 0.73 | 0.74 | 0.72 | 0.95 | 0.95 | 0.93 | 0.73 | 0.72 | 0.74 | 0.72 |
|  | Free amino acid concentration | 8.15 | 8.20 | 8.08 | 6.99 | 7.05 | 6.90 | 8.14 | 8.06 | 8.19 | 8.06 |
| Calculated value | Asp/K | 0.85 | 0.85 | 0.85 | 0.26 | 0.26 | 0.26 | 0.85 | 0.85 | 0.85 | 0.85 |
|  | Asp/N | 1.28 | 1.27 | 1.29 | 0.39 | 0.39 | 0.39 | 1.28 | 1.29 | 1.27 | 1.29 |
| Evaluation | Salty taste | 4 | 4 | 4 | 4 | 4 | 4 | 4 | 4 | 4 | 4 |
|  | Bitter taste | 1 | 1 | 1 | 1 | 1 | 1 | 1 | 1 | 1 | 1 |
|  | Abnormal taste | 1 | 1 | 2 | 1 | 1 | 2 | 1 | 1 | 1 | 2 |
|  | Comprehensive evaluation | E | E | G | E | E | G | E | E | E | G |

(4) Test Examples 7-1 to 7-10

The aforementioned low salt soy sauce E was used as a base soy sauce. Potassium chloride, a flavor improver, a food material having an antihypertensive effect, an amino acid seasoning, and the like, were added thereto, so as to prepare liquid seasonings with compositions shown in Table 5. The analysis of each component and sensory evaluation were carried out in the same manner as in Test Example 1. The results are shown in Table 5.

TABLE 5

|  |  | Test Example 7 Examples of the present invention ||||||||||
|---|---|---|---|---|---|---|---|---|---|---|---|
|  |  | 7-1 | 7-2 | 7-3 | 7-4 | 7-5 | 7-6 | 7-7 | 7-8 | 7-9 | 7-10 |
| Composition of seasoning (% by weight) | Low salt soy sauce A | 91.5 | 91.05 | 91.05 | 91.05 | 91.05 | 91.05 | 91.05 | 91.548 | 91.548 | 90.55 |
|  | Potassium chloride | 4 | 4 | 4 | 4 | 4 | 4 | 4 | 4 | 4 | 4 |
|  | Sodium 5'-ribonucleotide | 0.05 |  |  |  |  |  |  |  |  |  |
|  | Trisodium citrate |  | 0.5 |  |  |  |  |  |  |  |  |
|  | Magnesium chloride |  |  | 0.5 |  |  |  |  |  |  |  |
|  | Magnesium sulfate |  |  |  | 0.5 |  |  |  |  |  |  |
|  | Sodium sulfate |  |  |  |  | 0.5 |  |  |  |  |  |
|  | Maltitol |  |  |  |  |  | 0.5 |  |  |  |  |
|  | Reduced maltose starch syrup |  |  |  |  |  |  | 0.5 |  |  |  |
|  | Sodium glycyrrhizinate |  |  |  |  |  |  |  | 0.002 |  |  |
|  | Stevia |  |  |  |  |  |  |  |  | 0.002 |  |
|  | Whey mineral |  |  |  |  |  |  |  |  |  | 1.0 |
|  | Chlorogenic acid preparation | 1.25 | 1.25 | 1.25 | 1.25 | 1.25 | 1.25 | 1.25 | 1.25 | 1.25 | 1.25 |
|  | Sodium aspartate monohydrate | 2 | 2 | 2 | 2 | 2 | 2 | 2 | 2 | 2 | 2 |
|  | Sodium glutamate monohydrate | 1.2 | 1.2 | 1.2 | 1.2 | 1.2 | 1.2 | 1.2 | 1.2 | 1.2 | 1.2 |
| Analytical value (% by weight) | Sodium concentration | 3.34 | 3.31 | 3.31 | 3.31 | 3.31 | 3.31 | 3.31 | 3.33 | 3.33 | 3.30 |
|  | Common salt concentration | 8.51 | 8.43 | 8.43 | 8.43 | 8.43 | 8.43 | 8.43 | 8.48 | 8.48 | 8.39 |
|  | Potassium concentration | 2.45 | 2.44 | 2.44 | 2.44 | 2.44 | 2.44 | 2.44 | 2.45 | 2.45 | 2.44 |
|  | Nitrogen concentration excluding nitrogen from (C) and (E) | 1.63 | 1.63 | 1.63 | 1.63 | 1.63 | 1.63 | 1.63 | 1.63 | 1.63 | 1.62 |
|  | Glutamic acid concentration | 1.86 | 1.85 | 1.85 | 1.85 | 1.85 | 1.85 | 1.85 | 1.86 | 1.86 | 1.85 |
|  | Aspartic acid concentration | 2.09 | 2.08 | 2.08 | 2.08 | 2.08 | 2.08 | 2.08 | 2.09 | 2.09 | 2.08 |
|  | Acidic amino acid concentration | 3.95 | 3.94 | 3.94 | 3.94 | 3.94 | 3.94 | 3.94 | 3.95 | 3.95 | 3.93 |
|  | Basic amino acid concentration | 0.73 | 0.73 | 0.73 | 0.73 | 0.73 | 0.73 | 0.73 | 0.73 | 0.73 | 0.72 |
|  | Free amino acid concentration | 0.73 | 8.13 | 8.13 | 8.13 | 8.13 | 8.13 | 8.13 | 8.16 | 8.16 | 8.10 |
| Calculated value | Asp/K | 0.85 | 0.85 | 0.85 | 0.85 | 0.85 | 0.85 | 0.85 | 0.85 | 0.85 | 0.85 |
|  | Asp/N | 1.28 | 1.28 | 1.28 | 1.28 | 1.28 | 1.28 | 1.28 | 1.28 | 1.28 | 1.29 |

TABLE 5-continued

| | | Test Example 7 Examples of the present invention | | | | | | | | | |
|---|---|---|---|---|---|---|---|---|---|---|---|
| | | 7-1 | 7-2 | 7-3 | 7-4 | 7-5 | 7-6 | 7-7 | 7-8 | 7-9 | 7-10 |
| Evaluation | Salty taste | 4 | 4 | 4 | 4 | 4 | 4 | 4 | 4 | 4 | 4 |
| | Bitter taste | 1 | 1 | 1 | 1 | 1 | 1 | 1 | 1 | 1 | 1 |
| | Abnormal taste | 1 | 1 | 1 | 1 | 1 | 1 | 1 | 1 | 1 | 1 |
| | Comprehensive evaluation | E | E | E | E | E | E | E | E | E | E |

From the above results, it was found that even in the case of a liquid seasoning, which has a low sodium concentration and into which a food material having an antihypertensive effect is mixed, the liquid seasoning is able to have a sufficient salty taste by adjusting the potassium concentration to the range in the invention of the present application and by using a flavor improver, and thus the liquid seasoning has a taste level sufficiently good for continual ingestion as soy sauce.

Test 8

Preparation of Soy Sauce

A commercially available low-salt soy sauce was vacuum-concentrated and treated with volatile water and salt to eventually give a high nitrogen low-salt soy sauce in which the nitrogen concentration is 1.8% by weight, the sodium concentration is 3.34% by weight (common salt concentration is 8.5% by weight), and the potassium concentration is 0.45% by weight. Green coffee bean extract (hereinafter "GCE"), supplied by T. Hasegawa Co., Ltd. under the name of Flavor Holder RC-30, was spray-dried to give chlorogenic acids (about 54% by weight). Thus, liquid seasonings were prepared and then subjected to a human clinical test.

[Test Subjects]

117 men (30-50 years old) with low-grade hypertension (systolic blood pressure: 140-159 mmHg; diastolic blood pressure: 90-99 mmHg) were requested to take part in this test. However, anyone falling under the following categories, such as one taking 15 cigarettes or more per day, one consuming 30 g of alcohol or more per day, one suffering from hepatic abnormality, and one suffering from kidney abnormality, was excluded.

[Test Methods]
[Consuming Method/Quantity]

Hot water (180 mL) was poured into a bowl in which soy sauce (10 g) and a freeze-dried ingredient (one selected from seaweeds, tofu and deep-fried tofu) had beforehand been mixed, and then consumed at breakfast. Specifically, this sample was adjusted so as to meet the conditions that the content of GCE in 10 g of soy sauce is 0 mg, 46 mg, 93 mg or 185 mg, and consumed thereafter by the aforementioned 117 men divided into four groups (Table 7).

[Measurement Method]

After each group had been allowed to sit on a chair for 10 minutes, the blood pressure of their right arm was measured

TABLE 6

| | | Placebo group | Test groups | | |
|---|---|---|---|---|---|
| | | GCE 0 mg | GCE 46 mg | GCE 93 mg | GCE 185 mg |
| Composition | High nitrogen low-salt soy sauce | 93.84 | 93.38 | 92.91 | 91.99 |
| (% by weight) | Potassium chloride | 4 | 4 | 4 | 4 |
| | Lactic acid | 0.45 | 0.45 | 0.45 | 0.45 |
| | Citric acid | 0.045 | 0.045 | 0.045 | 0.045 |
| | Malic acid | 0.045 | 0.045 | 0.045 | 0.045 |
| | DiSodium succinate | 0.08 | 0.08 | 0.08 | 0.08 |
| | DiSodium inosinate | 0.04 | 0.04 | 0.04 | 0.04 |
| | Sodium glutaminate | 0.5 | 0.5 | 0.5 | 0.5 |
| | Sodium aspartate | 1 | 1 | 1 | 1 |
| | Green coffee bean extract | — | 0.46 | 0.93 | 1.85 |
| | 1) | (0) | (0.25) | (0.50) | (1.00) |
| Analytical | Sodium concentration | 3.36 | 3.34 | 3.32 | 3.29 |
| value (% | Common salt concentration | 8.54 | 8.50 | 8.46 | 8.38 |
| by weight) | Potassium concentration | 2.52 | 2.52 | 2.52 | 2.52 |
| | Nitrogen concentration excluding nitrogen from (C) and (E) | 1.81 | 1.80 | 1.80 | 1.78 |
| | Acidic amino concentration | 2.94 | 2.94 | 2.93 | 2.91 |
| | Basic acid amino concentration | 0.94 | 0.93 | 0.93 | 0.92 |
| | Aspartic acid concentration | 1.44 | 1.44 | 1.44 | 1.43 |
| | Glutamic acid concentration | 1.51 | 1.50 | 1.50 | 1.49 |
| Calculated | Asp/K | 0.57 | 0.57 | 0.57 | 0.57 |
| value | Asp/N | 0.80 | 0.80 | 0.80 | 0.80 |
| Nutrients per 10 g | Energy (kj) | 45.6 | 46.9 | 46.5 | 48.1 |
| of a test food | Carbohydrate (g) | 1.1 | 1.14 | 1.15 | 1.25 |
| | Lipid (g) | 0 | 0 | 0 | 0 |
| | Protein (g) | 1.01 | 1.02 | 1.02 | 1.03 |
| | Sodium (g) | 0.35 | 0.35 | 0.35 | 0.35 |
| | Potassium (g) | 0.25 | 0.25 | 0.25 | 0.25 |
| | Alcohol (g) | 0.35 | 0.36 | 0.35 | 0.35 |

Figure 3:
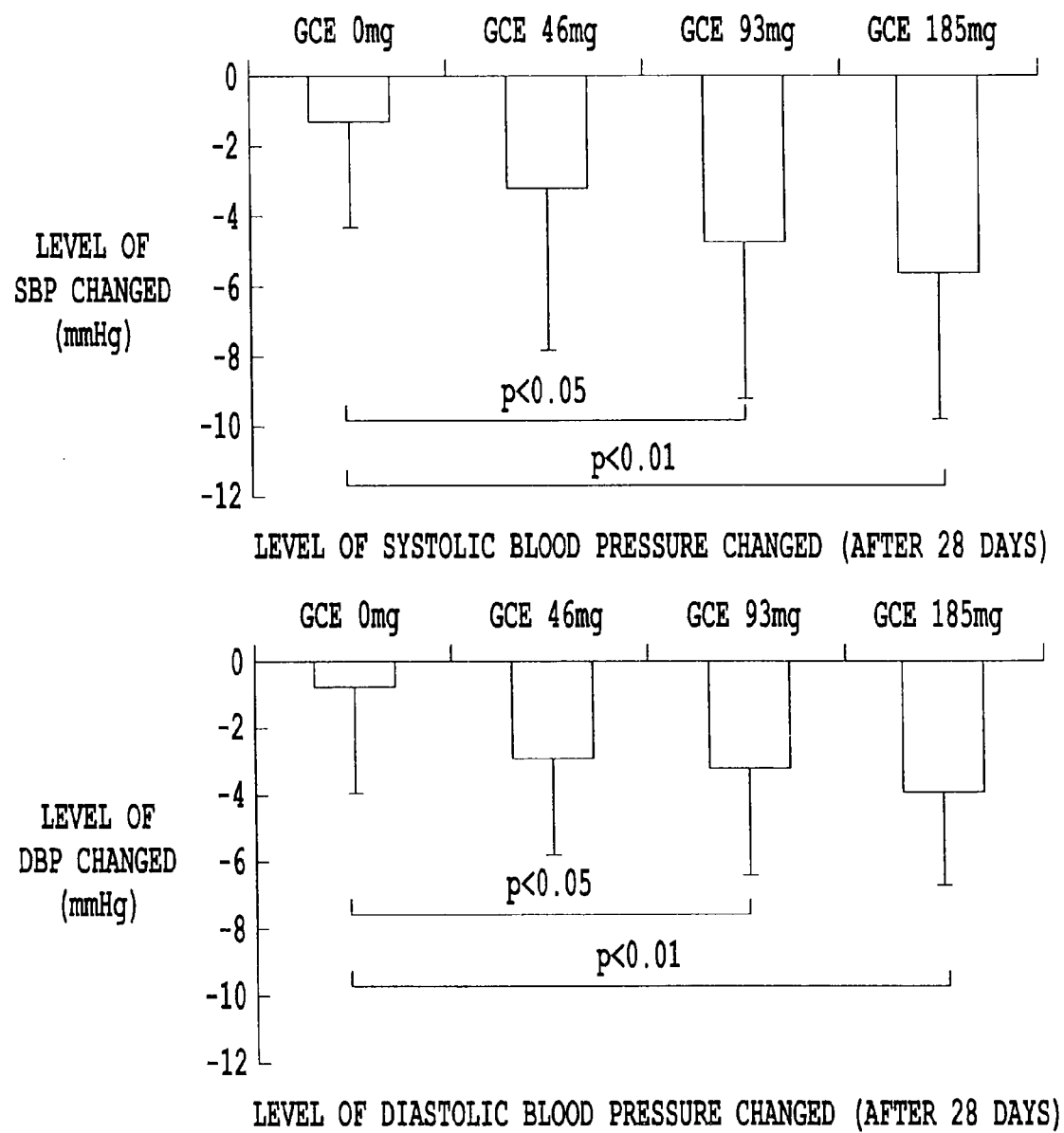
FIG. 3 shows the human systolic blood pressure and diastolic blood pressure which were measured 28 days after a continuous ingestion of the liquid seasoning of the present invention.

1) Chlorogenic acids 54%, Caffeine 12% three times by an automated sphygmomanometer, and both systolic blood pressure (SBP) and diastolic blood pressure (DBP) were compared. The median of each value was adopted as the measured value (FIG. 3).

[Statistical Processing]

The obtained data were subjected to a multiple comparison test using a statistical analysis software 'StatView Program' (version 5.0, SAS Institute Inc., Cary N.C.)

TABLE 7

|  |  | Placebo group | Test groups | | |
|---|---|---|---|---|---|
|  |  | GCE 0 mg | GCE 46 mg | GCE 93 mg | GCE 185 mg |
| Start of test | Test subjects | 29 | 29 | 28 | 31 |
|  | Age | 43.1 ± 9.1 | 42.9 ± 8.2 | 43.3 ± 8.3 | 43.4 ± 8.4 |
|  | Weight (kg) | 69.9 ± 10.7 | 73.9 ± 13.6 | 70.3 ± 8.1 | 73.6 ± 13.2 |
|  | BMI (kg/m$^2$) | 24.0 ± 3.1 | 25.2 ± 4.0 | 24.4 ± 2.6 | 25.1 ± 3.6 |
|  | SBP (mmHg) | 145.4 ± 5.5 | 145.9 ± 5.1 | 145.7 ± 5.0 | 146.0 ± 5.3 |
|  | DBP (mmHg) | 91.7 ± 2.5 | 92.1 ± 2.7 | 92.5 ± 2.7 | 92.5 ± 2.9 |
|  | Pulse (beats/min.) | 76.3 ± 8.9 | 79.6 ± 7.1 | 75.8 ± 7.7 | 79.5 ± 6.2 |
| End of test (After 28 th) | Weight (kg) | 69.7 ± 10.5 | 73.8 ± 13.4 | 70.2 ± 7.9 | 73.6 ± 13.1 |
|  | BMI (kg/m$^2$) | 23.9 ± 3.1 | 25.1 ± 4.0 | 24.4 ± 2.6 | 25.1 ± 3.6 |
|  | Level of SBP changed (mmHg) | −1.3 ± 3.0 | −3.2 ± 4.6 | −4.7 ± 4.5 | −5.6 ± 4.2 |
|  | Level of DBP changed (mmHg) | −0.8 ± 3.1 | −2.9 ± 2.9 | −3.2 ± 3.2 | −3.9 ± 2.8 |
|  | Pulse (beats/min.) | 75.8 ± 1.3 | 76.7 ± 1.1 | 77.1 ± 1.4 | 75.9 ± 1.2 |

All values represent 'mean ± SD'

[Analysis of Results]

As shown in Table 7, any of blood pressure, age, weight, BMI and the like was found not to be significantly different among the four groups (placebo group: GCE 0 mg, test groups: GCE 46 mg, 93 mg and 185 mg) at the start of the test.

As shown in FIG. 3, the level of SBP changed 28 days after the consumption was found to be −1.3±3.0 (GCE 0 mg) in respect of the placebo group, and to be −3.2±4.6 (GCE 46 mg), −4.7±4.5 (GCE 93 mg) and −5.6±4.2 (GCE 185 mg) in respect of the test groups. Thus, all of the four groups were found to have reduced their blood pressure. At the same time, the test groups given 93 mg or 185 mg of GCE were found to have reduced their blood pressure significantly, compared with the placebo group given 0 mg of GCE.

In addition, the level of DBP changed 28 days after the consumption was found to be −0.8±3.1 (GCE 0 mg) in respect of the placebo group, and to be −2.9±2.9 (GCE 46 mg), −3.2±3.2 (GCE 93 mg) and −3.9±2.8 (GCE 185 mg) in respect of the test groups. Thus, all of the four groups were found to have reduced their blood pressure. At the same time, the test groups given 93 mg or 185 mg of GCE were found to have reduced their blood pressure significantly, compared with the placebo group given 0 mg of GCE.

As evidenced from the above results, it has been found that the liquid seasoning of the present invention has an advantageous effect to reduce blood pressure when consumed. Also, from the results of the statistical analysis it has been confirmed that if more than 93 mg of GCE (50 mg of chlorogenic acids) is added to soy source, it is possible to obtain enough effect to reduce blood pressure by consuming it in a quantity of 10 g per day for a period of 1 month, compared with the placebo group.

What is claimed is:

1. A low salt soy sauce, comprising components (A) to (C):
   (A) sodium in an amount of up to 3.55% by weight;
   (B) potassium in an amount of 0.5% to 4.2% by weight, and
   (C) a food material having an antihypertensive effect, in an amount of 0.05% to 10% by weight, wherein the food material comprises an effective amount of at least one peptide having angiotensin converting enzyme inhibitory activity,
   wherein said at least one peptide having angiotensin converting enzyme inhibitory activity is selected from the group consisting of a peptide obtained from milk, a salt of a peptide obtained from milk, a peptide obtained from cereal, a salt of a peptide obtained from cereal, a peptide obtained from fish, and a salt of a peptide obtained from fish;
   wherein a remaining portion of the low salt soy sauce excluding component (C) is adapted by incorporation of a substance other than component (C) to have a nitrogen content (D) of 1.6% to 2% by weight, % by weight being based on a total weight of the low salt soy sauce.

2. A low salt soy sauce according to claim 1, wherein said at least one peptide having angiotensin converting enzyme inhibitory activity comprises a peptide obtained from corn cereal wherein said peptide obtained from corn cereal has a molecular weight of 200 Da to 4,000 Da.

3. A low salt soy sauce according to claim 1, wherein said at least one peptide having angiotensin converting enzyme inhibitory activity comprises a peptide obtained from cereal and said cereal comprises corn protein and wherein said corn protein is treated with an alkaline protease to obtain a treated peptide having a molecular weight between of 200 Da to 4,000 Da.

4. A low salt soy sauce according to claim 1, wherein said at least one peptide having angiotensin converting enzyme inhibitory activity comprises a peptide obtained from fish wherein said peptide obtained from fish has a molecular weight between of 200 Da to 10,000 Da.

5. A low salt soy sauce according to claim 4, wherein said peptide obtained from fish is obtained by treating a protein of a fish selected from the group consisting of mackerel, oceanic bonito, tuna and saury with protease.

6. A low salt soy sauce according to claim 4, wherein said peptide obtained from fish is obtained by treating a protein of oceanic bonito with protease.

7. A low salt soy sauce according to claim 1, further comprising component (E) as a flavor improver which is at least one member selected from the group consisting of an organic acid, an organic acid salt, an inorganic acid salt, an inorganic ammonium salt, a sweetener, whey mineral, a starch hydrolysate, a plant extract, and polysaccharide, and wherein a remaining portion of the low salt soy sauce excluding components (C) and (E) is adapted by incorporation of a substance other than components (C) and (E) to have a nitrogen content (D) of 1.6% to 2% by weight based on the total weight of the low salt soy sauce.

8. A low salt soy sauce according to claim 7, wherein said substance other than components (C) and (E) comprises an amino acid, so that the remaining portion of the low salt soy sauce excluding components (C) and (E) has a nitrogen content (D) of 1.6% to 2% by weight based on the total weight of the low salt soy sauce.

9. A low salt soy sauce according to claim 1, comprising more than 2% by weight of an acidic amino acid and/or more than 1% by weight of a basic amino acid, % by weight being based on a total weight of the low salt soy sauce.

10. A low salt soy sauce according to claim 1, comprising 1% to 3% by weight of aspartic acid and 1% to 2% by weight of glutamic acid, wherein a weight ratio of said aspartic acid to said potassium (B) is 0.25 or greater, % by weight being based on a total weight of the low salt soy sauce.

* * * * *